United States Patent [19]

Caldwell et al.

[11] Patent Number: 5,679,700
[45] Date of Patent: Oct. 21, 1997

[54] SUBSTITUTED PHOSPHINIC ACID-CONTAINING PEPTIDYL DERIVATIVES AS ANTIDEGENERATIVE AGENTS

[75] Inventors: Charles G. Caldwell, Scotch Plains; Philippe L. Durette, New Providence; Joung L. Goulet; William K. Hagmann, both of Westfield; Soumya P. Sahoo, Old Bridge, all of N.J.

[73] Assignee: Merck & Co., Inc., Rahway, N.J.

[21] Appl. No.: 555,535

[22] Filed: Nov. 9, 1995

Related U.S. Application Data

[63] Continuation of Ser. No. 256,217, filed as PCT/US93/00381, Jan. 15, 1993, abandoned, which is a continuation-in-part of Ser. No. 821,113, Jan. 15, 1992, abandoned.

[51] Int. Cl.$^6$ .............................. A61K 31/40; C07F 9/30
[52] U.S. Cl. .................... 514/416; 514/417; 514/422; 514/429; 514/399; 514/418; 514/419; 548/413; 548/414; 548/415; 548/481; 548/472; 548/491; 548/112; 549/58; 549/5; 549/220; 549/48; 549/221; 546/145; 546/117; 544/243; 544/337; 568/15; 558/170
[58] Field of Search ...................... 514/399, 416, 514/419, 417, 422, 428; 548/481, 472, 491, 112, 414, 415, 413; 549/58, 5, 220, 218, 221; 546/145, 117; 544/243, 337; 568/15; 558/170

[56] References Cited

U.S. PATENT DOCUMENTS

| | | | |
|---|---|---|---|
| 4,511,504 | 4/1985 | McCullugh et al. | 260/112.5 |
| 4,568,666 | 2/1986 | McCullugh et al. | 514/20 |
| 4,771,037 | 9/1988 | Roberts et al. | 514/18 |
| 4,885,283 | 12/1989 | Broadhurst et al. | 514/78 |
| 4,935,404 | 6/1990 | Hunter et al. | 514/19 |
| 4,937,243 | 6/1990 | Markwell et al. | 514/237.8 |
| 5,006,651 | 4/1991 | Broadhurst et al. | 540/463 |

FOREIGN PATENT DOCUMENTS

| | | |
|---|---|---|
| 0 156 322 | 10/1985 | European Pat. Off. |
| 0 209 848 | 1/1987 | European Pat. Off. |
| 0 210 545 | 2/1987 | European Pat. Off. |
| 0 232 027 | 8/1987 | European Pat. Off. |
| 0 276 436 | 8/1988 | European Pat. Off. |
| 0 497 192 | 8/1992 | European Pat. Off. |
| WO 93/14112 | 7/1993 | WIPO |

OTHER PUBLICATIONS

Grobelny, et al., Biochemistry vol. 28, pp. 4948–4951 (1989).

D.T. Parker, et al., Ciba–Geigy Corporation, Pharmaceuticals Division, "CGS27023A: A Novel, Potent, and Orally Active Matrix Metalloprotease Inhibitor", presented at Inflammation Research Assoc., 7th Intl. Conf., Sep. 25–29, 1994 at Whitehaven PA.

Eversole, et al., Presentation at 207th ACS Natl Mtg, San Diego, CA Mar. 13–17, 1994, "Development of Stromelysin INhibitors".

Caldwell, et al.,Submitted Nov. 26, 1995 to Bioorg. Med. Chem. Lett., "Phosphinic Acid Inhibitors of Matrix Metalloproteinases".

Grobelny, et al., Biochemical & Biophysical Research Comm., vol. 169, No. 3, pp. 1111–1116 (1990).

Birketal-Hansen, et al., Critical Rev. In Oral Biology and Medicine, vol. 4, No. 2, pp. 197–250 (1993).

Vincenti, et al., Arthritis & Rheumatism, vol. 37, pp. 1115–1126 (1994).

Goulet et al., Bioorg. Med. Lett., 4(10), 1221–4 1994.

*Primary Examiner*—Joseph McKane
*Assistant Examiner*—Richard S. Myers, Jr.
*Attorney, Agent, or Firm*—Curtis C. Panzer; David L. Rose

[57] ABSTRACT

Novel phosphinic acid-containing peptidyl compounds of formula I are found to be useful inhibitors of matrix metalloendoproteinase-mediated diseases including osteoarthritis, rheumatoid arthritis, septic arthritis, tumor invasion in certain cancers, periodontal disease, corneal ulceration, proteinuria, dystrophobic epidermolysis bullosa, and coronary thrombosis associated with atherosclerotic plaque rupture. These inhibitors may also be useful in preventing the pathological sequelae following a traumatic injury that could lead to permanent disability. These compounds may also have utility as a means for birth control by preventing ovulation or implantation.

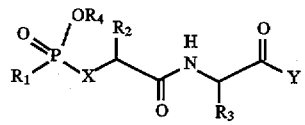

I

21 Claims, No Drawings

SUBSTITUTED PHOSPHINIC ACID-CONTAINING PEPTIDYL DERIVATIVES AS ANTIDEGENERATIVE AGENTS

RELATED U.S. APPLICATION DATA

This Application is a continuation of U.S. application Ser. No. 08/256,217 filed Jul. 5, 1994 (abandoned) which is in the National Filing of PCT application U.S. Pat. No. 93/00381 (WO 93/14112) filed Jan. 5, 1993, which is a continuation-in-part of U.S. Ser. No. 07/821,113, filed Jan. 15, 1992 (abandoned).

BACKGROUND OF THE INVENTION

This invention relates to substituted phosphinic acid-containing peptidyl derivatives of formula I useful in the treatment of matrix metalloendoproteinase mediated diseases including osteoarthritis, rheumatoid arthritis, septic arthritis, tumor invasion in certain cancers, periodontal disease, corneal ulceration, proteinuria, dystrophobic epidermolysis bullosa, and coronary thrombosis associated with atherosclerotic plaque rapture.

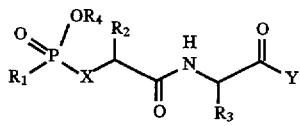

I

These inhibitors may also be useful in preventing the pathological sequelae following a traumatic injury that could lead to permanent disability. These compounds may also have utility as a means for birth control by preventing ovulation or implantation.

The disability observed in osteoarthritis (OA) and rheumatoid arthritis (RA) is largely due to the loss of articular cartilage. No existing therapeutic agent prevents the attrition of articular cartilage in these diseases.

"Disease modifying antirheumatic drugs" (DMARDs), i.e., agents capable of preventing or slowing the ultimate loss of joint function in OA and RA, are widely sought. Generic nonsteroidal antiinflammatory drugs (NSAIDs) may be combined with such agents to provide some relief from pain and swelling.

Stromelysin (aka. proteoglycanase, matrix metalloproteinase-3, MMP-3, procollagenase activator, "transin"), collagenase (aka. interstitial collagenase, matrix metalloproteinase-1, MMP-1) and gelatinase (type-IV collagenase, matrix metalloproteinase-2, MMP-2, 72 kDa-gelatinase) are metalloendoproteinases secreted by fibroblasts and chondrocytes, and are capable of degrading the major connective tissue components of articular cartilage. Elevated levels of stromelysin and collagenase have been detected in joints of arthritic humans and animals: K. A. Hasty, R. A. Reife, A. H. Kant, J. M. Stuart, "The role of stromelysin in the cartilage destruction that accompanies inflammatory arthritis", Arthr. Rheum., 33, 388–97 (1990); S. M. Krane, E. P. Amento, M. B. Goldring, S. R. Goldring, and M. L. Stephenson, "Modulation of matrix synthesis and degradation in joint inflammation", The Control of Tissue Damage", A. B. Glauert (ed.), Elsevier Sci. Publ., Amsterdam, 1988, Ch. 14, pp 179–95; A. Blanckaert, B. Mazieres, Y. Eeckhout, G. Vaes, "Direct extraction and assay of collagenase from human osteoarthrtic cartilage", Clin. Chim. Acta, 185 73–80 (1989). Each enzyme is secreted from these cells as an inactive proenzyme which is subsequently activated. There is evidence that stromelysin may be the in vivo activator for collagenase, implying a cascade for degradative enzyme activity: A. Ho, H. Nagase, "Evidence that human rheumatoid synovial matrix metalloproteinase 3 is an endogenous activator of procollagenase", Arch Biochem Biophys., 267, 211–16 (1988); G. Murphy, M. I. Crockett, P. E. Stephens, B. J. Smith, A. J. P. Docherty, "Stromelysin is an activator of procollagenase", Biochem. J., 248, 265–8 (1987). Inhibiting stromelysin will limit the activation Of collagenase as well as prevent the degradation of proteoglycan.

That stromelysin inhibition may be effective in preventing articular cartilage degradation has been demonstrated in vitro by measuring the effect of matrix metalloendoproteinase inhibitors on proteoglycan release from rabbit cartilage explants: C. B. Caputo, L. A. Sygowski, S. P. Patton, D. J. Wolanin, A. Shaw, R. A. Roberts, G. DiPasquale, J. Orthopaedic Res., 6, 103–8 (1988).

There is an extensive literature on the involvement of these metalloproteinases in arthritis, but there is very little to guide one in developing a specific inhibitor for each enzyme. In preliminary studies of rabbit proteoglycanase with substrates and inhibitors, little was found to indicate the enzyme's requirements for hydrolysis or inhibition beyond a preference for hydrophobic residues at the $P_1'$ position of this enzyme: A. Shaw, R. A. Roberts, D. J. Wolanin, "Small substrates and inhibitors of the metalloproteoglycanase of rabbit articular chondrocytes", Adv. Inflam. Res., 12, 67–79 (1988). More extensive studies with a series of substrates revealed that stromelysin will tolerate nearly every amino acid residue around the scissile bond: G. B. Fields, H. Brikedal-Hansen, H. E. Van Wart, unpublished results presented at the Matrix Metalloproteinase Conference, September 1989, Sandestin Fla.

Human rheumatoid synovial collagenase has been shown to share ~50% homology with human stromelysin: S. E. Whitham, G. Murphy, P. Angel, H. J. Rahmsdorf, B. J. Smith, A. Lyons, T. J. R. Harris, J. J. Reynolds, P. Herrlich, A. J. P. Docherty, "Comparison of human stromelysin and collagenase by cloning and sequence analysis", Biochem. J., 240, 913–6 (1986). Many collagenase inhibitors have been designed around the cleavage site of the α-chain sequence of collagen: W. H. Johnson, N. A. Roberts, N. Brokakoti, "Collagenase inhibitors: their design and potential therapeutic use", J. Enzyme Inhib., 2,1–22 (1987). One such inhibitor, N-[3-(benzyloxycarbonyl)amino-1-carboxy-n-propyl]-L-leucyl-O-methyl-L-tyrosine, N-methylamide, prepared at G. D. Searle, Inc., and shown to be a potent inhibitor of human rheumatoid synovial collagenase ($IC_{50}$= 0.8 μM), was also found to inhibit rabbit bone proteoglycanase ($IC_{50}$=0.5 μM): J.-M. Delaisse, Y. Eeckhout, C. Sear, A. Galloway, K. McCullagh, G. Vaes, "A new synthetic inhibitor of mammalian tissue collagenase inhibits bone resorption in culture", Biochem. Biophys. Res. Commun., 133, 483–90 (1985).

Gelatinase (MR~72,000) has been isolated from rheumatoid fibroblasts: Y. Okada, T. Morodomi, J. J. Enghild, K. Suzuki, A. Yasui, I. Nakanishi, G. Salvesen, H. Nagase, "Matrix metalloproteinase 2 from human rheumatoid synovial fibroblasts", Eur. J., Biochem., 194, 721–30 (1990). The synthesis of the proenzyme is not coordinately regulated with the other two metalloproteinases and its activation may also be different. The role of gelatinase in the tissue destruction of articular cartilage appears different from the other two enzymes and, therefore, its inhibition may provide additional protection from degradation.

As appreciated by those of skill in the art, the significant proportion of homology between human synovial collagenase, human stromelysin, and gelatinase leads to the possibility that a compound that inhibits one enzyme may inhibit them all.

Compounds that inhibit collagenase, which possess structural portions akin to those of the instant invention, include those encompassed by U.S. Pat. No. 4,885,283.

The applicants believe that stromelysin and collagenase inhibitors will have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case, J. Sano, R. Lafyatis, E. F. Remmers, G. K. Kumkumian, R. L. Wilder, "Transin/stromelysin expression in the synovium of rats with experimental erosive arthritis", J. Clin Invest., 84, 1731–40 (1989); R. J. Williams, R. L. Smith, D. J. Schurman, "Septic Arthritis: Staphylococcal induction of chondrocyte proteolytic activity", Arthr. Rheum., 33, 533–41 (1990).

The applicants also believe that inhibitors of stromelysin, collagenase, and gelatinase will be useful to control tumor metastasis, optionally in combination with current chemotherapy and/or radiation. See L. M. Matrisian, G. T. Bowden, P. Krieg, G. Furstenberger, J. P. Briand, P. Leroy, R. Breathnach, "The mRNA coding for the secreted protease transin is expressed more abundantly in malignant than in benign tumors", Proc. Natl. Acad. Sci., USA, 83, 9413–7 (1986); S. M. Wilhelm, I. E. Collier, A. Kronberger, A. Z. Eisen, B. L. Marmer, G. A. Grant, E. A. Bauer, G. I. Goldberg, "Human skin fibroblast stromelysin: structure, glycosylation, substrate specificity, and differential expression in normal and tumorigenic cells", Ibid., 84, 6725–29 (1987); Z. Werb et al., "Signal Transduction through the Fibronectin Receptor Induces Collagenase and Stromelysin Gene Expression", J. Cell Biol., 109, 872–889 (1989); L. A. Liotta, C. N. Rao, S. H. Barsky, "Tumor invasion and the extracellular matrix", Lab. Invest., 49, 636–649 (1983); R. Reich, B. Stratford, K. Klein, G. R. Martin, R. A. Mueller, G. C. Fuller, "Inhibitors of collagenase IV and cell adhesion reduce the invasive activity of malignant tumor cells", in Metastasis: Ciba Foundation Symposium; Wiley, Chichester, 1988, pp. 193–210.

Secreted proteinases such as stromelysin, collagenase, and gelatinase play an important role in processes involved in the movement of cells during metastatic tumor invasion. Indeed, there is also evidence that the matrix metalloendoproteinases are overexpressed in certain metastatic tumor cell lines. In this context, the enzyme functions to penetrate underlying basement membranes and allow the tumor cell to escape from the site of primary tumor formation and enter circulation. After adherence to blood vessel walls, the tumor cells use these same metalloendoproteinases to pierce underlying basement membranes and penetrate other tissues, thereby leading to tumor metastasis. Inhibition of this process would prevent metastasis and improve the efficacy of current treatments with chemotherapeutics and/or radiation.

These inhibitors would also be useful for controlling periodontal diseases, such as gingivitis. Both collagenase and stromelysin activities have been isolated from fibroblasts isolated from inflammed gingiva: V. J. Uitto, R. Applegren, P. J. Robinson, "Collagenase and neutral metalloproteinase activity in extracts of inflammed human gingiva", J. Periodontal Res., 16, 417–424 (1981). Enzyme levels have been correlated to the severity of gum disease: C. M. Overall, O. W. Wiebkin, J. C. Thonard, "Demonstration of tissue collagenase activity in vivo and its relationship to inflammation severity in human gingiva", J. Periodontal Res., 22, 81–88 (1987).

Proteolytic processes have also been observed in the ulceration of the cornea following alkali burns: S. I. Brown, C. A. Weller, H. E. Wasserman, "Collagenolytic activity of alkali-burned corneas", Arch. Opthalmol., 81, 370–373 (1969). Mercapto-containing peptides do inhibit the collagenase isolated from alkali-burned rabbit cornea: F. R. Burns, M. S. Stack, R. D. Gray, C. A. Paterson, Invest. Opthalmol., 30, 1569–1575 (1989). Treatment of alkali-burned eyes or eyes exhibiting corneal ulceration as a result of infection with inhibitors of these metalloendoproteinases in combination with sodium citrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine; W. H. Baricos, G. Murphy, Y. Zhou, H. H. Nguyen, S. V. Shah, "Degradation of glomerular basement membrane by purified mammalian metalloproteinases", Biochem. J., 254, 609–612 (1988). Proteinuria, a result of glomerular disease, is excess protein in the urine caused by increased permeability of the GBM to plasma proteins. The underlying causes of this increased GBM permeability are unknown, but proteinases including stromelysin may play an important role in glomerular diseases. Inhibition of this enzyme may alleviate the proteinura associated with kidney malfunction.

Inhibition of stromelysin activity may also prevent the rupture of atherosclerotic plaques leading to coronary thrombosis. The tearing or rupture of atherosclerotic plaques is the most common event initiating coronary thrombosis. Destabilization and degradation of the connective tissue matrix surrounding these plaques by proteolytic enzymes or cytokines released by infiltrating inflammatory cells have been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery: A. M. Henney, P. R. Wakeley, M. J. Davies, K. Foster, R. Hembry, G. Murphy, S. Humphries, "Localization of stromelysin gene expression in atherosclerotic plaques by in situ hybridization", Proc. Nat'l. Acad. Sci. USA, 88, 8154–8158 (1991). Inhibition of stromelysin by these compounds may aid in preventing or delaying the degradation of the connective tissue matrix that stabilizes the atherosclerotic plaques, thereby preventing events leading to acute coronary thrombosis.

It is also believed that specific inhibitors of stromelysin and collagenase would be useful as birth control agents. There is evidence that expression of metalloendoproteinases, including stromelysin and collagenase, is present in unfertilized eggs and zygotes and cleavage stages and increased at the blastocyst stage of fetal development and with endoderm differentiation: C. A. Brenner, R. R. Adler, D. A. Rappolee, R. A. Pedersen, Z. Werb, "Genes for extracellular matrix-degrading metalloproteinases and their inhibitor, TIMP, are expressed during early mammalian development", Genes & Develop., 3, 848–59 (1989). By analogy to tumor invasion, a blastocyst may express metalloproteinases in order to penetrate the extracellular matrix of the uterine wall during implantation. Inhibition of stromelysin and collagenase during these early developmental processes would presumably prevent normal embryonic development and/or implantation in the uterus. Such intervention would constitute a novel method of birth control. In addition there is evidence that collagenase is important in ovulation processes. In this example, a covering of collagen over the apical region of the follicle must be penetrated in order for the ovum to escape. Collagenase has been detected during this process and an inhibitor has been shown to be effective in preventing ovulation: J. F. Woessner, N. Morioka, C. Zhu, T. Mukaida, T. Butler, W. J. LeMaire "Connective tissue breakdown in ovulation", Steroids, 54, 491–499 (1989). There may also be a role for stromelysin activity during ovulation: C. K. L. Too, G. D. Bryant-Greenwood, F. C. Greenwood, "Relaxin increases the release of plasminogen activator, collagenase, and proteoglycanase from rat granulosa cells in vitro", Endocrin., 115, 1043–1050 (1984).

Collagenolytic and stromelysin activity have also been observed in dystrophobic epidermolysis bullosa: A. Kronberger, K. J. Valle, A. Z. Eisen, E. A. Bauer, J. Invest. Dermatol., 79 208–211 (1982); D. Sawamura, T. Sugawara, I. Hashimoto, L. Bruckmer-Tuderman, D. Fujimoto, Y. Okada, N. Utsumi, H. Shikata, Biochem. Biophys, Res. Comm., 174, 1003–8 (1991). Inhibition of metalloendoproteinases should limit the rapid destruction of connective components of the skin.

In addition to extracellular matrix comprising structural components, stromelysin can degrade other in vivo substrates, including the inhibitors $\alpha_1$-proteinase inhibitor and may therefore influence the activities of other proteinases, such as elastase. Inhibition of these enzymes may potentiate the antiproteinase activity of these endogenous inhibitors.

SUMMARY OF THE INVENTION

The invention encompasses novel phosphinic acid-containing peptidyl compounds of formula I, which are useful inhibitors of stromelysin, collagenase, and gelatinase-mediated diseases, including degenerative diseases (as defined herein) and certain cancers.

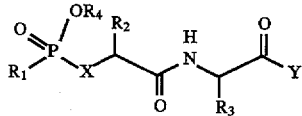

I

DETAILED DESCRIPTION OF THE INVENTION

The invention encompasses compounds of formula I

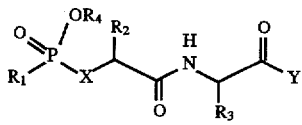

I or a pharmaceutically acceptable salt thereof wherein:
$R_1$ is substituted $C_{1-10}$alkyl, wherein the substituent is selected from the group consisting of:
(a) hydrogen,
(b) —C(O)OH,
(c) —C(O)OC$_{1-6}$alkyl,
(c) —C(O)O C$_{1-6}$alkylphenyl,
(d) —C(O)NH$_2$,
(e) —C(O)NHC$_{1-6}$alkyl,
(f) —C(O)N(C$_{1-6}$alkyl)$_2$, (g) —C(O)N(C$_{1-6}$alkyl)C$_{6-10}$aryl or —C(O)N(C$_{1-6}$alkyl)C$_{6-10}$arylC$_{1-6}$alkyl,
(h) —C(O)NHC$_{6-10}$aryl or —C(O)NHC$_{6-10}$arylC$_{1-6}$alkyl, wherein the aryl group is selected from the group consisting of
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) benzoxazolyl,
(24) isoxazolyl, and
(25) benzthiazolyl, and mono and di-substituted C$_{6-10}$aryl as defined above in items (1) to (25), wherein the substitutents are each independently hydrogen, C$_{1-6}$alkyl, halo, hydroxy, C$_{1-6}$alkylcarbonyl, carboxy;

(i)

wherein $R_a$ and $R_b$ are each independently hydrogen, NHC$_{1-6}$alkyl, NHC$_{6-10}$aryl, NHC$_{6-10}$arylC$_{1-6}$alkyl, OC$_{1-6}$alkyl, OC$_{6-10}$aryl, OC$_{6-10}$arylC$_{1-6}$alkyl, C$_{6-10}$aryl or C$_{6-10}$aryl-C$_{1-6}$alkyl, wherein the C$_{6-10}$aryl may be mono or di-substituted as defined above; or substituted C$_{1-6}$alkyl wherein the substitutent is selected from hydroxy and halo, or wherein $R_a$ and $R_b$ are joined such that together with the nitrogen and carbon atoms to which they are attached, there is formed a lactam or a benzolactam wherein the lactam portion thereof is a ring of up to 8 atoms, and said lactam or benzolactam has a single hereto atom;

(j)

wherein $R_c$ and $R_d$ are each independently hydrogen, C$_{6-10}$aryl, or C$_{6-10}$aryl C$_{1-6}$alkyl or wherein the C$_{6-10}$aryl may be mono or di-substituted as defined above; or substituted C$_{1-6}$alkyl wherein the substitutent is selected from hydroxy and halo, or wherein $R_c$ and $R_d$ are joined such that together with the nitrogen and carbon atoms to which they are attached, there is formed a cyclic imide or benzocyclic imide wherein the imide portion thereof is a ring of up to 8 atoms, and said cyclic imide or benzocyclic imide has a single hereto atom;

(k) 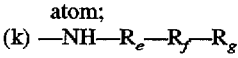

wherein $R_e$ is a single bond or an amino acid of the formula

—COCH(Z)NH— or Re is selected from the group consisting of glycine, alanine, leucine, isoleucine, norleucine, phenylalanine, tyrosine, lysine, arginine, histidine, aspartic acid, asparagine, glutamic acid, glutamine, serine and threonine;
$R_f$ is a single bond, acetyl, benzoyl, benzyloxycarbonyl, phthalimido or $R_f$ is an amino acid of the formula

—COCH(Z')NH— wherein
Z and Z' are each independently selected from the group consisting of
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino $C_{1-6}$alkyl,
(g) aminocarbonyl $C_{1-6}$alkyl,
(h) mono- or di-$C_{1-6}$alkyl amino $C_{1-6}$alkyl,
(i) guanidino $C_{1-6}$alkyl,
(j) substituted phenyl $C_{1-6}$alkyl, wherein the substitutent is hydrogen, hydroxy, carboxy, or $C_{1-4}$alkyl,
(k) substituted indolyl $C_{1-6}$alkyl, wherein the substitutent is hydrogen, hydroxy, carboxy, or $C_{1-4}$alkyl,
(l) substituted imidazolyl $C_{1-6}$alkyl wherein the substitutent is hydrogen, hydroxy, carboxy, or $C_{1-4}$alkyl;
or Rf is selected from the group consisting of glycine, alanine, proline;
$R_g$ is acetyl, benzoyl, benzyloxycarbonyl, p-toluenesulfonyl, or t-butyloxycarbonyl;
$R_2$ is $CHR_hR_i$ wherein
$R_h$ is
(a) H
(b) $C_{1-3}$alkyl, or
(c) hydroxyl,
(d) $C_{6-10}$aryl; and
$R_i$ is $C_{6-10}$aryl-$C_{0-2}$alkyl or substituted $C_{6-10}$aryl-$C_{0-2}$alkyl wherein the substituent is $C_{1-3}$alkyl or hydroxy, and wherein
the aryl group in definition $R_h$ and $R_i$ is independently selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl, and
(23) isoxazolyl,
and mono and di-substituted $C_{6-10}$aryl as defined above in items (1) to (23) wherein the substitutents are independently $C_{1-6}$alkyl, halo, hydroxy, and $C_{1-6}$alkylcarbonyl;

$R_3$ is $C_{1-4}$alkyl or an amino acid of the formula

—COCH(Z")NH— where
Z" is selected from the group consisting of,
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino $C_{1-6}$alkyl,
(g) aminocarbonyl $C_{1-6}$alkyl,
(h) mono- or di-$C_{1-6}$alkylamino $C_{1-6}$alkyl,
(i) guanidino $C_{1-6}$alkyl,
(j) substituted phenyl $C_{1-6}$alkyl, wherein the substitutent is hydrogen, hydroxy, carboxy, or $C_{1-4}$alkyl,
(k) substituted indolyl-$C_{1-6}$alkyl, wherein the substitutent is hydrogen, hydroxy, carboxy, or $C_{1-4}$alkyl,
(l) substituted imidazolyl-$C_{1-6}$alkyl wherein the substitutent is hydrogen, hydroxy, carboxy, or $C_{1-4}$alkyl;
or wherein said amino acid is selected from the group consisting of glycine, alanine, leucine, isoleucine, norleucine, phenylalanine, tyrosine, lysine, arginine, histidine, aspartic acid, asparagine, glutamic acid, glutamine, serine, and threonine;
$R_4$ is
(a) H,
(b) $CH(R_j)O—C(O)—R_k$
wherein $R_j$ is hydrogen, $C_{1-6}$alkyl, $C_{6-10}$aryl, or $C_{6-10}$aryl-$C_{1-6}$alkyl and $R_k$ is $C_{1-6}$alkyl, $C_{6-10}$aryl, $C_{6-10}$aryl-$C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl, and
(23) isoxazolyl,
and mono and di-substituted $C_{6-10}$aryl as defined above in items (1) to (23) wherein the substitutents are independently $C_{1-6}$alkyl, halo, hydroxy, and $C_{1-6}$alkylcarbonyl;
X is $CH_2$ or $CH(C_{1-6}$alkyl); and Y is

wherein $R_5$ and $R_6$ are each individually selected from the group consisting of
(a) H,
(b) $C_{1-10}$alkyl,
(c) $C_{6-10}$aryl or $C_{6-10}$aryl$C_{1-6}$alkyl,
wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carboxazolyl,
(23) isoxazolyl,
(24) benzthiazolyl, and
(25) benzoxazolyl;

and $C_{6-10}$aryl and mono and di-substituted $C_{6-10}$aryl as defined above in items (1) to (25) wherein the substitutents are independently. $C_{1-6}$alkyl, halo, hydroxy, $C_{1-6}$alkyloxy, $C_{1-6}$alkylcarbonyl, carboxy and $C_{1-6}$alkylcarbonyloxy.

One genus of this embodiment is the compounds wherein:

$R_1$ is $C_{1-6}$alkyl or substituted $C_{1-6}$alkyl, wherein the substituent is selected from the group consisting of:
(a) hydrogen,
(b) carboxy,
(c) —C(O)NH$_2$,
(d) —C$_{6-10}$aryl or C$_{6-10}$aryl C$_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl, and
(9) indolyl, and mono and di-substituted $C_{6-10}$aryl as immediately defined in definitions (1) to (9) above wherein the substitutents are independently $C_{1-6}$alkyl, halo, hydroxy, and carbonyl$C_{1-6}$alkyl, carboxy;

wherein $R_a$ and $R_b$ are each independently hydrogen, $C_{6-10}$ aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and mono and di-substituted $C_{6-10}$ aryl as defined in items (1) to (9) above; or substituted $C_{1-6}$alkyl wherein the substitutent is selected from hydroxy and halo, or wherein $R_a$ and $R_b$ are joined together to form a ring as defined above;

wherein $R_c$ and $R_d$ are each independently hydrogen, $C_{6-10}$aryl and mono and di-substituted $C_{6-10}$aryl as defined above; or substituted $C_{1-6}$alkyl wherein the substitutent is selected from hydroxy, halo, and phenyl, or wherein $R_c$ and $R_d$ are joined such that together with the nitrogen and carbon atoms to which they are attached, there is formed a cyclic imide or benzocyclic imide wherein the imide portion thereof is a ring of up to 8 atoms, and said cyclic imide or benzocyclic imide has a single hereto atom;

(g) —NH—$R_e$—$R_f$—$R_g$
wherein Re is an amino acid of the formula

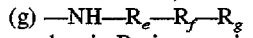

or Re is selected from the group consisting of glycine, alanine, leucine, isoleucine, norleucine, phenylalanine, tyrosine, lysine, arginine, histidine, aspartic acid, asparagine, glutamic acid, glutamine, serine, threonine;

$R_f$ is a single bond, acetyl, benzoyl, benzyloxycarbonyl, phthalimido or $R_f$ is an amino acid of the formula

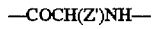

wherein
Z and $Z^1$ are each independently selected from the group consisting of
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino $C_{1-6}$alkyl,
(g) aminocarbonyl $C_{1-6}$alkyl,
(h) mono- or di-$C_{1-6}$alkyl amino $C_{1-6}$alkyl,
(i) guanidino $C_{1-6}$alkyl,
(j) substituted phenyl $C_{1-6}$alkyl, wherein the substitutent is hydrogen, hydroxy, carboxy, or $C_{1-4}$alkyl,
(k) substituted indolyl $C_{1-6}$alkyl, wherein the substitutent is hydrogen, hydroxy, carboxy, or $C_{1-4}$alkyl,
(l) substituted imidazolyl $C_{1-6}$alkyl wherein the substitutent is hydrogen, hydroxy, carboxy, or $C_{1-4}$alkyl; or Rf is selected from the group consisting of glycine, alanine, and proline;

$R_g$ is acetyl, benzoyl, benzyloxycarbonyl, p-toluenesulfony, or t-butyloxycarbonyl.

One class of this genus is the compounds wherein:

$R_2$ is $CHR_hR_i$ wherein $R_h$ is
(a) H,
(b) $C_{1-3}$alkyl, or
(c) hydroxyl;

$R_i$ is $C_{6-10}$aryl-$C_{0-2}$alkyl or substituted $C_{6-10}$aryl $C_{0-2}$alkyl, wherein
the substituent is $C_{1-3}$alkyl or hydroxy, and wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and mono and di-substituted $C_{6-10}$aryl as defined above in items (1) to (9) wherein the substituents are independently $C_{1-6}$alkyl, halo, hydroxy, and carbonyl$C_{1-6}$alkyl.

A sub-class of this class is the compounds wherein:

wherein $R_5$ is hydrogen, and $R_6$ is selected from the group consisting of
(a) $C_{1-10}$alkyl, or
(b) $C_{6-10}$aryl, or $C_{6-10}$aryl$C_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
(10) pyridyl.

Exemplifying the invention are the following compounds:
(a) (2-(((4-(1,3-Dihydro-1,3-dioxo-2H-isoindol-2-yl)-butyl)hydroxyphosphinyl) methyl)-4-phenylbutanoyl)-L-leucine N-phenylamide
(b) (2-(((4-(1,3-Dihydro-1-oxo-2H-isoindol-2-yl)butyl)-hydroxyphosphinyl)methyl)-4-phenylbutanoyl)-L-leucine N-phenylamide
(c) (2-(((4-(1,3-Dihydro-1-oxo-2H-isoindol-2-yl)butyl) (2-methyl-1-(1-oxopropoxy) propoxy)phosphinyl) methyl)-4-phenylbutanoyl)-L-leucine N-phenylamide
(d) (2-((Hydroxy(methyl)phosphinyl)methyl)-4-phenylbutanoyl)-L-leucine N-phenylamide
(e) [[Hydroxy[1(R)-[N-(N-acetyl-L-prolyl-L-alanyl)-amino]-ethyl]-phosphinyl]-methyl]-4-phenyl-butanoyl-L-leucyl N-phenylamide
(f) [Hydroxy-[N-(N-(benzoyl)-L-prolyl) aminobutyl] phosphinyl]methyl]-4-phenylbutanoyl-L-leucine N-phenyl-amide
(g) [Hydroxy-[2-Methylpropyloxycarbonylaminobutyl]-phosphinyl]methyl]-4-phenylbutanoyl-L-leucine N-phenylamide; and
(h) [Hydroxy-[1-Methylethylaminocarbonylaminobutyl]-phosphinyl]methyl]-4-phenylbutanoyl-L-leucine N-phenylamide This invention also concerns pharmaceutical compositions and methods of treatment of stromelysin-mediated or implicated disorders or diseases (as described above) in a patient (including man and/or mammalian animals raised in the dairy, meat, or fur industries or as pets) in need of such treatment comprising administration of the stromelysin inhibitors of formula I as the active constituents.

Similarly, this invention also concerns pharmaceutical compositions and methods of treatment of matrix metalloproteinase-mediated or implicated disorders or diseases (as described above) in a patient in need of such treatment comprising administration of the inhibitors of formula I as the active constituents.

Compounds of the instant invention are conveniently prepared using the procedures described generally below and more explicitly described in the Example section thereafter.

As shown in Scheme 1, Compound A is converted into Compound C via ester exchange followed by Michael addition. Thereafter, Compound D having the desired stereochemistry at the indicated center is obtained by basic hydrolysis of Compound C followed by optical resolution by use of a chiral amine. Nucleophilic displacement of the halide in $R^1X$ wherein X is chloro, bromo, or iodo, with Compound D results in the formation of the phosphinic acid E. Thereafter, removal of the benzyl ester group by hydrogenolysis followed by peptide coupling results in Compound G. Thereafter, Compound G may be further transformed into the desired final product. For instance, in Example 2, the compound of formula G is protected as the methyl phosphinate ester, the N-phthaloyl group is removed by hydrazinolysis, and the resulting amine further derivatized, and the methyl phosphinate ester group removed in the final step.

In Scheme 2, Compound H is alkylated with $R_4Cl$ (except where $R_4$ is hydrogen) to form the phosphinate ester I.

Scheme 3 summarizes access to compounds having alternative definitions of $R_1$, in particular, those comprising one or more amino acids. As shown, Michael addition of Compound I to Compound J affords Compound K. After removal of the t-butyl ester group, Compound L undergoes a peptide coupling reaction to form Compound M. After removal of the N-terminal protecting group, further peptide coupling yields the compound of formula O, which after final deprotection results in Compound P.

In an alternative route, Compound K may be deprotected at $R'_1$. Subsequent peptide coupling and final deprotection may then be achieved in the manner shown in Scheme 1.

SCHEME 1

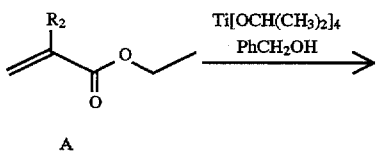

A

SCHEME 1 -continued

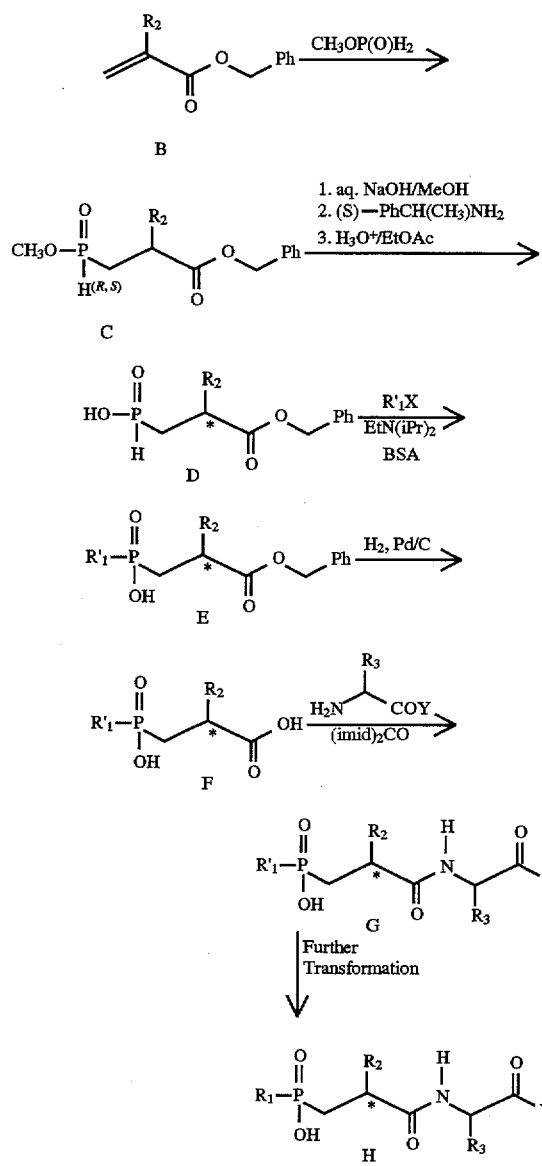

SCHEME 2

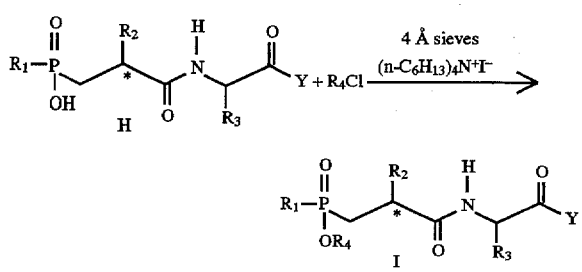

SCHEME 3

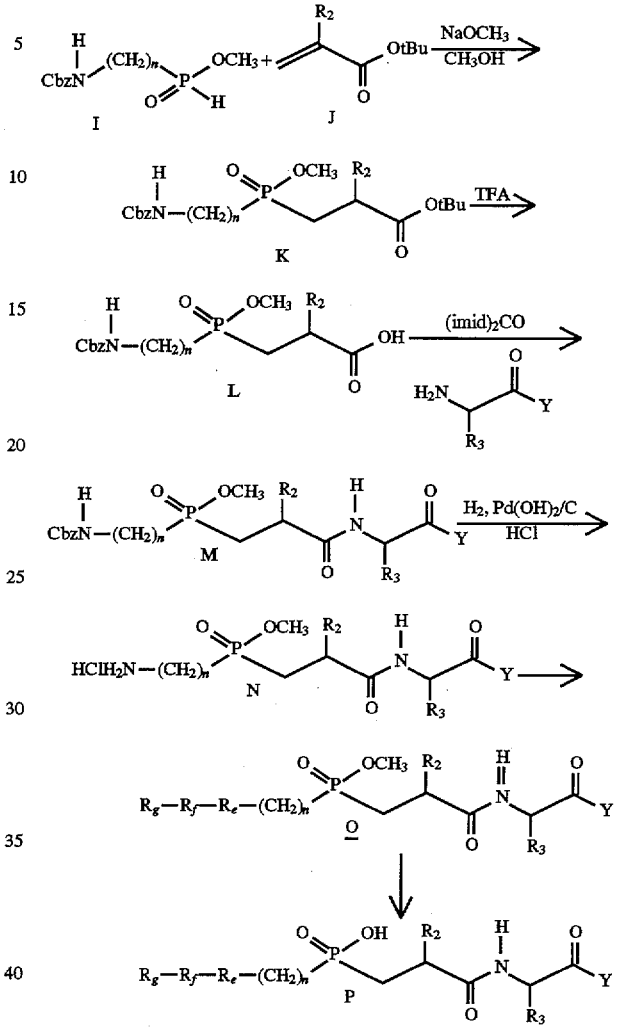

A representative number of compounds of the instant invention of the formula I are shown below to exhibit in vitro inhibitory activities with respect to stromelysin, collagenase, or gelatinase. In particular, the compounds of formula I have been shown to inhibit the hydrolysis of Substance P (that is, Arg-Pro-Lys-Pro-Gln-Gln-Phe-Phe-Gly-Leu-Met-$NH_2$) by stromelysin employing the method described in detail in the literature: R. Harrison, J. Teahan, R. Stein, "A semicontinuous, high-performance liquid chromatography-based assay for stromelysin", Analytical Biochem, 180, 110–113 (1989). Compounds of formula I were shown to inhibit the cleavage of a fluorogenic peptide, DNP-Pro-Leu-Gly-Leu-Trp-Ala-(D)-Arg-$NH_2$ by collagenase and gelatinase employing the previously described method: M. S. Stack, R. D. Gray, "Comparison of Vertebrate Collagenase and Gelatinase Using a New Fluorogenic Substrate Peptide", J. Biol. Chem., 264, 4277–81 (1989).

TABLE I $$\text{Structure I: } R_1-P(=O)(OR_4)-X-CH(R_2)-C(=O)-NH-CH(R_3)-C(=O)-Y$$

| R₁ | X | R₂ | R₃ | Y | R4 | STROMELYSIN Ki, μM (±SE) | COLLAGENASE Ki, μM (±SE) Human Fibroblast | GELATINASE Ki, μM (±SE) |
|---|---|---|---|---|---|---|---|---|
| (CH₂)₄N—Phth | CH₂ | (CH₂)₂Ph | (S)-i-C₄H₉ | NHPh | H | 0.0014(.0003) | 1.0 | 0.026(.005) |
| CH₃ | CH₂ | (CH₂)₂Ph | (S)-i-C₄H₉ | NHPh | H | 1.5(.1) | | 0.57(.01) |
| (R)—CH(CH₃)—NH—Ala—Pro—Ac | CH₂ | (CH₂)₂Ph | (S)-i-C₄H₉ | NHPh | H | 0.0061(.0016) | 2.9(.2) | 0.0026(.0007) |
| CH₂CH₂CO₂CH₃ | CH₂ | (CH₂)₂Ph | (S)-i-C₄H₉ | NHPh | H | 0.52(.06) | 0 ≅ 10 | 1.3(.1) |
| (CH₂)₄N—ProCOPh | CH₂ | (CH₂)₂Ph | (S)-i-C₄H₉ | NHPh | H | 0.013(.003) | 10 ≅ 10 | 0.0021(.0004) |
| (CH₂)₄N—CO₂-i-C₄H₄ | CH₂ | (CH₂)₂Ph | (S)-i-C₄H₉ | NHPh | H | 0.019(.002) | 0 ≅ 10 | 0.034(.004) |
| (CH₂)₄NCHCONH-i-C₃H₇ | CH₂ | (CH₂)₂Ph | (S)-i-C₄H₉ | NHPh | H | 0.022(001) | 0 ≅ 10 | 0.0056(.0007) |

TABLE II $$\text{Structure I: } R_1-P(=O)(OR_4)-X-CH(R_2)-C(=O)-NH-CH(R_3)-C(=O)-Y$$

| R₁ | X | R₂ | R₃ | Y |
|---|---|---|---|---|
| (CH₂)₄Ph | CH₂ | CH₂Ph | (S)-i-C₄H₉ | NHCH₂Ph |
| (CH₂)₄N—Phth | CH₂ | CH₂Ph | (S)-i-C₄H₉ | NHCH₂Ph |
| (CH₂)₄Ph | CH₂ | CH₂Ph | (S)—CH₂Ph | NHCH₂Ph |
| (CH₂)₄N—Phth | CH₂ | CH₂Ph | (S)-i-C₄H₉ | NHPh |
| (CH₂)₄Ph | CH₂ | (CH₂)₂Ph | (S)-i-C₄H₉ | NHCH₂Ph |
| (CH₂)₄Ph | CH₂ | (CH₂)₂Ph | (S)-i-C₄H₉ | NHPh |
| (CH₂)₄N—Phth | CH₂ | (CH₂)₂Ph | (S)-i-C₄H₉ | NHPh |
| (R)—CH(CH₃)—CH₂—NH—Cbz | CH₂ | (CH₂)₂Ph | (S)-i-C₄H₉ | NHPh |
| CH₂—NH—Cbz | CH₂ | (CH₂)₂Ph | (S)-i-C₄H₉ | NHPh |
| CH₃ | CH₂ | (CH₂)₂Ph | (S)-i-C₄H₉ | NHPh |
| (R)—CH(CH₃)—NH—Ala—Pro—Ac | CH₂ | (CH₂)₂Ph | (S)-i-C₄H₉ | NHPh |
| CH₂—NH—Gly—Gly—Phth | CH₂ | (CH₂)₂Ph | (S)-i-C₄H₉ | NHPh |
| (R)—CH(CH₃)—Gly—Phth | CH₂ | (CH₂)₂Ph | (S)-i-C₄H₉ | NHPh |
| (R)—CH(CH₃)—NH—COPh | CH₂ | (CH₂)₂Ph | (S)-i-C₄H₉ | NHPh |
| CH₂—NH—COPh | CH₂ | (CH₂)₂Ph | (S)-i-C₄H₉ | NHPh |
| CH₂—NH—Ala—Cbz | CH₂ | (CH₂)₂Ph | (S)-i-C₄H₉ | NHPh |
| (S)—CH(CH₃)—NH—Cbz | CH₂ | (CH₂)₂Ph | (S)-i-C₄H₉ | NHPh |
| (R)—CH(CH₃)—NH—Ala—Ac | CH₂ | (CH₂)₂Ph | (S)-i-C₄H₉ | NHPh |
| CH₂—NH—Lys—Cbz | CH₂ | (CH₂)₂Ph | (S)-i-C₄H₉ | NHPh |
| (R)—CH(CH₃)—NH—Ala—Pro—COPh | CH₂ | (CH₂)₂Ph | (S)-i-C₄H₉ | NHPh |
| CH₂—NH—Ala—Pro—Ac | CH₂ | (CH₂)₂Ph | (S)-i-C₄H₉ | NHPh |
| CH₂—NH—nLeu—Cbz | CH₂ | (CH₂)₂Ph | (S)-i-C₄H₉ | NHPh |
| CH₂—NH—COCH₂Ph | CH₂ | (CH₂)₂Ph | (S)-i-C₄H₉ | NHPh |
| CH₂CH₂CO₂-t-C₄H₉ | CH₂ | (CH₂)₂Ph | (S)-i-C₄H₉ | NHPh |
| CH₂—NH—Phe—Cbz | CH₂ | (CH₂)₂Ph | (S)-i-C₄H₉ | NHPh |
| (R)—CH(CH₃)—NH—Ala—Ala—Ac | CH₂ | (CH₂)₂Ph | (S)-i-C₄H₉ | NHPh |
| CH₂CH₂CON—HCH₂Ph | CH₂ | (CH₂)₂Ph | (S)-i-C₄H₉ | NHPh |
| CH₂CH₂CON— | CH₂ | (CH₂)₂Ph | (S)-i-C₄H₉ | NHPh |

TABLE II-continued

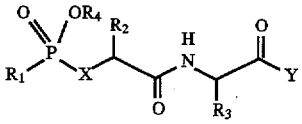

| $R_1$ | X | $R_2$ | $R_3$ | Y |
|---|---|---|---|---|
| $H(CH_2)_2Ph$ | | | | |
| $(CH_2)_4N-Phth$ | $CH(CH_3)$ | $(CH_2)_2Ph$ | (S)-i-$C_4H_9$ | NHPh |
| $CH_2-NH-Gly-Cbz$ | $CH_2$ | $(CH_2)_2Ph$ | (S)-i-$C_4H_9$ | NHPh |
| $CH_2CH_2CO_2-CH_3$ | $CH_2$ | $(CH_2)_2Ph$ | (S)-i-$C_4H_9$ | NHPh |
| $CH_2-NH-Glu-Cbz$ | $CH_2$ | $(CH_2)_2Ph$ | (S)-i-$C_4H_9$ | NHPh |
| $CH_2-NH-His-Cbz$ | $CH_2$ | $(CH_2)_2Ph$ | (S)-i-$C_4H_9$ | NHPh |
| $CH_2-NH-Gln-Cbz$ | $CH_2$ | $(CH_2)_2Ph$ | (S)-i-$C_4H_9$ | NHPh |
| $CH_2-NH-Ala-Pro-COPh$ | $CH_2$ | $(CH_2)_2Ph$ | (S)-i-$C_4H_9$ | NHPh |
| $(CH_2)_4N-Pro-Ac$ | $CH_2$ | $(CH_2)_2Ph$ | (S)-i-$C_4H_9$ | NHPh |
| $(CH_2)_4N-COPh$ | $CH_2$ | $(CH_2)_2Ph$ | (S)-i-$C_4H_9$ | NHPh |
| $(CH_2)_4N-COCH_2Ph$ | $CH_2$ | $(CH_2)_2Ph$ | (S)-i-$C_4H_9$ | NHPh |
| $CH_2-NH-Tyr-Cbz$ | $CH_2$ | $(CH_2)_2Ph$ | (S)-i-$C_4H_9$ | NHPh |
| $(CH_2)_4N-Pro-COPh$ | $CH_2$ | $(CH_2)_2Ph$ | (S)-i-$C_4H_9$ | NHPh |
| $CH(CH_2Ph)-NH-Cbz$ | $CH_2$ | $(CH_2)_2Ph$ | (S)-i-$C_4H_9$ | NHPh |
| $CH_2-NH-CO$-t-$CHCHPh$ | $CH_2$ | $(CH_2)_2Ph$ | (S)-i-$C_4H_9$ | NHPh |
| $CH_2-NH-CO(CH_2)_2Ph$ | $CH_2$ | $(CH_2)_2Ph$ | (S)-i-$C_4H_9$ | NHPh |
| $CH_2CH_2CONHPh$ | $CH_2$ | $(CH_2)_2Ph$ | (S)-i-$C_4H_9$ | NHPh |
| $CH_2-NH-CO(CH_2)_4Ph$ | $CH_2$ | $(CH_2)_2Ph$ | (S)-i-$C_4H_9$ | NHPh |
| $CH_2-NH-COCH_2$-1-Adamantyl | $CH_2$ | $(CH_2)_2Ph$ | (S)-i-$C_4H_9$ | NHPh |
| $CH_2-NH-COC_2H_5$ | $CH_2$ | $(CH_2)_2Ph$ | (S)-i-$C_4H_9$ | NHPh |
| $CH_2-NH-CO(CH_2)_3Ph$ | $CH_2$ | $(CH_2)_2Ph$ | (S)-i-$C_4H_9$ | NHPh |
| $CH_2-NH-(R)-Ala-Cbz$ | $CH_2$ | $(CH_2)_2Ph$ | (S)-i-$C_4H_9$ | NHPh |
| $(CH_2)_4N-Phth(H_2)$ | $CH_2$ | $(CH_2)_2Ph$ | (S)-i-$C_4H_9$ | NHPh |
| $(CH_2)_4N-CO_2CH_2Ph$ | $CH_2$ | $(CH_2)_2Ph$ | (S)-i-$C_4H_9$ | NHPh |
| $(CH_2)_4N-CO_2CH_3$ | $CH_2$ | $(CH_2)_2Ph$ | (S)-i-$C_4H_9$ | NHPh |
| $(CH_2)_4N-(R)-Pro-COPh$ | $CH_2$ | $(CH_2)_2Ph$ | (S)-i-$C_4H_9$ | NHPh |
| $(CH_2)_4N-CO_2C_2H_5$ | $CH_2$ | $(CH_2)_2Ph$ | (S)-i-$C_4H_9$ | NHPh |
| $CH_2CH_2CONH-(CH_2)_3Ph$ | $CH_2$ | $(CH_2)_2Ph$ | (S)-i-$C_4H_9$ | NHPh |
| $(CH_2)_4NH_2$ | $CH_2$ | $(CH_2)_2Ph$ | (S)-i-$C_4H_9$ | NHPh |
| $(CH_2)_4N-CO_2Ph$ | $CH_2$ | $(CH_2)_2Ph$ | (S)-i-$C_4H_9$ | NHPh |
| $(CH_2)_4N-CO_2$-i-$C_4H_9$ | $CH_2$ | $(CH_2)_2Ph$ | (S)-i-$C_4H_9$ | NHPh |
| $CH_2-NH-CSNH(CH_2)_2Ph$ | $CH_2$ | $(CH_2)_2Ph$ | (S)-i-$C_4H_9$ | NHPh |

This invention also relates to a method of treatment for patients (including man and/or mammalian animals raised in the dairy, meat, or fur industries or as pets) suffering from disorders or diseases which can be attributed to matrix metalloproteinases as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of stromelysin, collagenase, and/or gelatinase such as found in certain metastatic tumor cell lines.

For the treatment of rheumatoid arthritis, osteoarthritis, and in diseases and indications resulting from the over-expression of matrix metalloproteinases such as found in certain metastatic tumor cell lines or other diseases mediated by these enzymes, the compounds of formula (I) may be administered orally; topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,255,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic, parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I)

are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms. per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples are intended to illustrate the preparation of compounds of formula I, and as such are not intended to limit the invention as set forth in the claims appended thereto.

EXAMPLE 1

(2-(((4-(1,3-Dihydro-1,3-dioxo-2H-isoindol-2-yl)butyl) hydroxyphosphinyl)methyl)-4-phenylbutanoyl)-L-leucine N-phenylamide Step A: Benzyl 2-methylene-4-phenylbutanoate Titanium(IV) isopropoxide (225 μL, 215 mg, 0.87 mmol) was added to a solution of ethyl 2-methylene-4-phenylbutanoate[1] (1.00 g, 4.90 mmol) and benzyl alcohol (8.0 mL, 8.4 g, 77 mmol)[2]. The reaction was warmed in an oil bath for 12 h at 100° C. followed by 3 h at 110° C. The reaction flask was evacuated (25 mm Hg) for 5–10 min at 1-h intervals during the first 5 h, then maintained at 25 mm Hg for the remaining reaction time. After the reaction had cooled to room temperature, concentrated aqueous hydrochloric acid (5 mL) was added and the mixture was extracted with 1:1 ether/hexane (30 mL). The organic layer was washed with saturated aqueous sodium bicarbonate (10 mL) and saturated aqueous sodium chloride (10 mL), dried (magnesium sulfate), filtered, and evaporated at 1.0 mm Hg with bath temperature up to 80° C. The resulting crude product (1.64 g) was purified by flash column chromatography on silica gel (10 g) eluting with 5% ether/hexane to give 1.22 g (94% yield) of benzyl 2-methylene-4-phenylbutanoate as a colorless oil.

1 Fraisse-Jullien, R.; Fréjaville, C. *Bull. Soc. Chim. Fr.* 1970, 219–230.

2 Seebach, D.; Hungerbühler, E.; Naef, R.; Schnurrenberger, P.; Weldmann, B.; Züger, M. *Synthesis* 1982, 138–141.

Step B: Benzyl 2-((methoxyphosphinyl)methyl)-4-phenylbutanoate

Trimethyl orthoformate (11.0 mL, 10.7 g, 101 mmol) was added to anhydrous hypophosphorous acid[3] (4.0 mL, 6.0 g, 90 mmol) and the solution was stirred for 1.5 h at room temperature. In a separate flask, N,N,N',N'-tetramethylguanidine (1.50 mL, 1.38 g, 12.0 mmol) was added to benzyl 2-methylene-4-phenyl-butanoate (3.99 g, 15.0 mmol) and the solution was cooled to 0° C. by an ice bath. An portion of the methyl hypophosphite solution (12.0 mL, d=1.04 g/mL, approx. 68 mmol) was added over 1 h. The ice bath was removed and the solution was stirred an additional 1.25 h. The reaction was diluted with ethyl acetate (150 mL) and washed with 2N aqueous hydrochloric acid (50 mL), water (50 mL), and saturated aqueous sodium chloride (50 mL). The aqueous layers were extracted in succession with ethyl acetate (50 mL). The organic layers were dried (sodium sulfate), decanted, and evaporated. After drying overnight under vacuum, the crude product was 5.19 g (100% yield) of viscous colorless oil.

3 S. J. Fitch, *J. Am. Chem. Soc.* 1964, 86, 61–64 and M. J. Broadhurst, B. K. Handa, W. H. Johnson, G. Lawton, and P. J. Machin, Eur. patent 276436-A (1988).

Step C: (±)-Benzyl 2-((hydroxyphosphinyl)methyl)-4-phenylbutanoate

A solution of benzyl 2-((methoxyphosphinyl)methyl)-4-phenylbutanoate (4.02 g, 11.6 mmol) in methanol (20 mL) was cooled in an ice bath and 2.5N aqueous sodium hydroxide (5.1 mL, 12.8 mmol) was added over 10 min. The resulting solution was stirred at 0° C. for 45 min before being diluted with water (150 mL) and washed with a mixture of ether (75 mL) and hexane (25 mL). The aqueous layer was washed with hexane (75 mL), acidified by the addition of 2N aqueous hydrochloric acid (20 mL), and extracted with ethyl acetate (2×75 mL). The ethyl acetate layers were washed in succession with saturated aqueous sodium chloride (50 mL), dried (sodium sulfate), decanted, and evaporated. The residue was dried overnight under vacuum to give crude (±)-benzyl 2-((hydroxyphosphinyl) methyl)-4-phenylbutanoate as 3.67 g of colorless oil (95% yield).

Step D: (+)-Benzyl 2-((hydroxyphosphinyl)methyl)-4-phenylbutanoate (S)-α-Methylbenzylamine (1.42 mL, 1.34 g, 11.1 mmol) was added to a solution of (±)-2-((hydroxyphosphinyl) methyl)-4-phenylbutanoate (3.65 g, 11.0 mmol) in ethyl acetate (50 mL) in ethyl acetate (50 mL). The solution was seeded and allowed to stand at room temperature for 4 h. The crystals were separated by filtration, washed with ethyl acetate (20 mL), and dried under vacuum to give 2.12 g of the salt. This material was dissolved in a mixture of ethyl acetate (90 mL) and 95% ethanol (12 mL) at 90° C., then allowed to cool to room temperature and to stand overnight. Filtration and drying under vacuum yielded 1.202 g of white crystals: $[\alpha]_{365}$ −11.2° (c=0.57, 95% ethanol). This salt was partitioned between ethyl acetate (75 mL) and 2N aqueous hydrochloric acid (25 mL). The ethyl acetate layer was washed with 2N aqueous hydrochloric acid (25 mL) saturated aqueous sodium chloride (25 mL), dried (sodium sulfate), decanted, and evaporated. The resulting colorless oil was seeded and dried under vacuum to give 864 mg (24% recovery) (+)-benzyl 2-((hydroxyphosphinyl)methyl)-4-phenylbutanoate as colorless crystals: $[\alpha]_{365}$ +7.6° (c=0.52, 95% ethanol).

Step E: N-(4-Bromo-2-butenyl)phthalimide

Potassium phthalimide (4.60 g, 24.8 mmol) was added in four portions at 15-min intervals to a solution of 1,4- dibromo-2-butene (10.60 g, 49.5 mmol) in dimethylformamide (20 mL) and the resulting mixture was stirred overnight at room temperature. The mixture was concentrated under reduced pressure and the residue was partitioned between dichloromethane (25 mL) and 2N aqueous hydrochloric acid (25 mL). The aqueous layer was-extracted with dichloromethane (2×25 mL) and the organic layers were washed in succession with saturated aqueous sodium chloride (20 mL), dried (sodium sulfate), filtered, and evaporated. The crude product was purified by flash column chromatography silica gel (150 g) eluting with 50% dichlormethane/hexane increasing to 100% dichlormethane to yield 5.12 g (74% yield) of white crystalline product.

4 Wright, W. B., Jr.; Press, J. B.; Chan, P. S.; Marisco, H. W.; Haug, M. F.; Lucas, J.; Tauber, J.; Tomcufcik, A. S. *J. Med. Chem.* 1986, 29, 523–530.

Step F: Benzyl 2-(((4-(1,3-dihydro-1,3-dioxo-2H-isoindol-2-yl)-2-butenyl)hydroxyphosphinyl)methyl)-4-phenylbutanoate Dichloromethane (30 mL) was added to (+)-benzyl 2-((hydroxyphosphinyl)methyl)-4-phenylbutanoate (8.10 g, 24.4 mmol) and 4Å molecular sieves (5.0 g). Diisopropylethylamine (4.70 mL, 3.49 g, 27.0 mmol) was added over 5 min. After cooling the reaction mixture in an ice bath, O,N-bis(trimethylsilyl)acetamide (17.7 mL, 14.6 g, 71.6 mmol) was added in one portion, followed in 10 min by N-(4-bromo-2-butenyl)phthalimide (8.80 g, 31.4 mmol). The mixture was allowed to slowly warm to room temperature and stirred for 20 h before being filtered. The sieve particles were rinsed with ethyl acetate (100 mL) and the filtrate was washed with 2N aqueous hydrochloric acid (2×50 mL) and saturated aqueous sodium chloride (25 mL). The aqueous layers were extracted in succession with ethyl acetate (50 mL). The organic layers were dried (sodium sulfate), decanted, and evaporated to give 15.66 g of almost colorless syrup containing benzyl 2-(((4-(1,3-dihydro-1,3-dioxo-2M-isoindol-2-yl)-2-butenyl)hydroxyphosphinyl)methyl)-4-phenylbutanoate.

Step G: 2-(((4-(1,3-Dihydro-1,3-dioxo-2H-isoindol-2-yl)butyl)hydroxyphosphinyl)methyl)-4-phenylbutanoic acid A portion (14.66 g) of the crude product from Step F was dissolved in 95% ethanol (125 mL). Catalyst (2.50 g of 20% palladium hydroxide on carbon) was added and the mixture was stirred under hydrogen (1 atm.) for 20 h at room temperature. The reaction mixture was filtered through a 2-cm pad of Celite with additional 95% ethanol (100 mL). Evaporation of the filtrate gave 12.55 g of thick orange syrup containing 2-(((4-(1,3-dihydro-1,3-dioxo-2H-isoindol-2-yl)butyl)hydroxyphosphinyl)methyl)-4-phenylbutanoic acid.

Step H: (2-(((4-(1,3-Dihydro-1,3-dioxo-2H-isoindol-2-yl)butyl)hydroxyphosphinyl)methyl)-4-phenylbutanoyl)-L-leucine N-phenylamide The crude product from Step G was dissolved in tetrahydrofuran (80 mL) and the solution was cooled in an ice bath. A slurry of 1,1'-carbonyldiimidazole (4.09 g, 25.2 mmol) in tetrahydrofuran (10 mL) was added over 10 min with additional tetrahydrofuran (3×5 mL) to complete the transfer. After 30 min, a solution of L-leucine N-phenylamide (5.60 g, 27.1 mmol) in tetrahydrofuran (10 mL) was added over 10 min with additional tetrahydrofuran (5 mL) to complete the transfer. The homogeneous solution was allowed to slowly warm to room temperature and stirred for 16 h. The mixture was concentrated on a rotary evaporator to remove most of the tetrahydrofuran and the residue was partitioned between ethyl acetate (150 mL) and 2N aqueous hydrochloric acid (75 mL). The ethyl acetate layer was washed with saturated aqueous sodium chloride (2×25 mL). The crystals which spontaneously formed in the organic layer were separated by filtration and partioned between chloroform (300 mL) and 2N aqueous hydrochloric acid, and the chlorform layer was washed with saturated aqueous sodium chloride (50 mL). The sodium chloride layer was extracted with chloroform (2×25 mL). The combined chlorform extracts were dried (magnesium sulfate), filtered, and evaporated. The residue was dissolved in boiling tetrahydrofuran (100 mL), allowed to cool to 25° C., evaporated to a mass of 40 g, and dissolved in ethyl acetate (150 mL). After 2 h at 25° C., the crystals were separated by filtration, washed with ethyl acetate (2×20 mL) and ether (20 mL), and dried under vacuum to give 6.17 g of almost colorless crystals. Evaporation of the mother liquor and recrystallization produced a second crop of 1.62 g (total yield 54% for steps F–H) of (2-(((4-(1,3-dihydro-1,3-dioxo-2H-isoindol-2-yl)butyl)hydroxyphosphinyl)methyl)-4-phenylbutanoyl)-L-leucine N-phenylamide.

Anal. Calcd for $C_{35}H_{42}N_3O_6P$: C, 66.55; H, 6.70; N, 6.65; P, 4.90. Found: C, 66.58; H, 6.64; N, 6.60; P, 5.05.

EXAMPLE 2

(2-(((4-(1,3-Dihydro-1-oxo-2H-isoindol-2-yl)butyl)hydroxyphosphinyl)methyl)-4-phenylbutanoyl)-L-leucine N-phenylamide

Step A: (2-(((4-(1,3-Dihydro-1,3-dioxo-2H-isoindol-2-yl)butyl)methoxyphosphinyl)methyl)-4-phenylbutanoyl)-L-leucine N-phenylamide A mixture of dichloromethane (100 mL) and (2-(((4-(1,3-dihydro-1,3-dioxo-2H-isoindol-2-yl)butyl)hydroxyphosphinyl)methyl)-4-phenylbutanoyl)-L-leucine N-phenylamide (2.00 g, 3.17 mmol) from Example 1 was warmed to give a clear solution which was then cooled in an ice bath. Diazomethane (0.3M solution in ether) was added until the yellow color persisted and the solution was stired 10 min longer. Glacial acetic acid (0.080 mL, 84 mg, 1.4 mmol) was added to give a colorless solution which was concentrated under vacuum. Methanol (100 mL) was added and the solution was evaporated again and dried under vacuum to give 2.09 g of crude product which was used in the next reaction without further purification.

Step B: (2-(((4-Aminobutyl)methoxyphosphinyl)methyl)-4-phenylbutanoyl)-L-leucine N-phenylamide Anhydrous hydrazine (0.21 mL, 214 mg, 6.7 mmol) was added to methanol (20 mL) containing the crude (2-(((4-(1,3-dihydro-1,3-dioxo-2H-isoindol-2-yl)butyl)methoxyphosphinyl)methyl)-4-phenylbutanoyl)-L-leucine N-phenylamide (2.09 g) from Step A. After 16 h of stirring at at room temperature, the mixture was filtered and the precipitate was washed with methanol (10 mL). The filtrate was evaporated to a mass of 7.6 g and filtered with additional methanol (5 mL) used to rinse the precipitate. Evaporation and drying under vacuum yielded 2.17 g of solid product containing 2-(((4-aminobutyl)methoxyphosphinyl)methyl)-4-phenylbutanoyl)-L-leucine N-phenylamide.

Step C: (2-(((4-(1,3-Dihydro-1-oxo-2H-isoindol-2-yl)butyl)methoxyphosphinyl)methyl)-4-phenylbutanoyl)-L-leucine N-phenylamide Crude 2-(((4-aminobutyl)methoxyphosphinyl)methyl)-4-phenylbutanoyl)-L-leucine anilide (0.70 from Step B was stirred with tetrahydrofuran (5.0 mL) containing diisopropylethylamine (0.20 mL, 148 mg, 1.15 mmol). Methyl 2-(bromomethyl)benzoate[5] (258 mg, 1.13 mmol) was added and the reaction was stirred for 24 h at room temperature. The mixture was diluted with ethyl acetate (50 mL) and washed with 2N aqueous hydrochloric acid (15 mL), saturated aqueous sodium bicarbonate (15 mL), and saturated aqueous sodium chloride. The aqueous layers were extracted in succession with ethyl acetate (25 mL) and the combined organic layers were dried (sodium sulfate) filtered, and evaporated. Purification by flash column chromatography on silica gel (18 g) eluting with 40% acetone/dichloromethane increasing to 60% acetone/dichloromethane gave 0.31 g of product yield for Steps A–C.

5 Danishefsky, S.; Bryson, T. A.; Puthenpurayil, J. *J. Org. Chem.* 1975, 40, 796–7.

Step D: (2-(((4-(1,3-Dihydro-1-oxo-2H-isoindol-2-yl)butyl)hydroxyphosphinyl)methyl)-4-phenylbutanoyl)-L-leucine N-phenylamide (2-(((4-(1,3-Dihydro-1-oxo-2H-isoindol-2-yl)butyl) methoxyphosphinyl)methyl)-4-phenylbutanoyl)-L-leucine N-phenylamide (0.31 g, 0.49 mmol) from Step C was dissolved in methanol (10 mL). The solution was cooled in an ice bath and 2N aqueous sodium hydroxide (5 mL, 10 mmol) was added. The solution was allowed to warm to room temperature and was stirred for an additional 12 h before being diluted with 2N aqueous hydrochloric acid (40 mL) and extracted with ethyl acetate (75 mL). The organic extract was washed with saturated aqueous sodium chloride (25 mL), dried (sodium sulfate), and evaporated. The crude product was purified by high pressure liquid chromatography on a 22 mm×25 cm reverse phase column (Whatman ODS-3, Partisil 10) eluting with 45% acetonitrile/55% water/0.05% trifluoroacetic acid (flow rate of 20 mL/min, detection at 250 nm). Evaporation of appropriate fractions gave 264 mg the desired product (88% yield) as a colorless brittle foam.

EXAMPLE 3

(2-(((4-(1,3-Dihydro-1-oxo-2H-isoindol-2-yl)butyl) (2-methyl-1-(1-oxopropoxy)propoxy)phosphinyl) methyl)-4-phenylbutanoyl)-L-leucine N-phenylamide 1-Chloroisobutyl propionate (0.20 mL) was added to a mixture of 4 Å molecular sieves (125 mg), tetra-n-hexylammonium iodide (40 mg, 0.083 mmol), and (2-(((4-(1,3-Dihydro-1-oxo-2H-isoindol-2-yl)butyl) hydroxyphosphinyl)methyl)-4-phenylbutanoyl)-L-leucine N-phenylamide (50 mg, 0.081 mmol).[6] The mixture was warmed in an oil bath at 65°–70° C. for 7 h, then allowed to stand at room temperature overnight. The mixture was diluted into ethyl acetate (25 mL) and washed with 2N aqueous hydrochloric acid (25 mL) and saturated aqueous sodium chloride, and the organic layer was dried (sodium sulfate), decanted, and evaporated. The crude product was purified by flash column chromatography on silica gel (3 g) eluting with 20% acetone/dichloromethane to give 19 mg. (32% yield) of (2-(((4-(1,3-dihydro-1-oxo-2H-isoindol-2-yl)butyl)(2-methyl-1-(1-oxopropoxy)propoxy)phosphinyl) methyl)-4-phenylbutanoyl)-L-leucine N-phenylamide.

6 Petrillo, E. W., Jr.; Karanewsky, D. S.; Thottahil, J. K.; Heikes, J. E.; Grosso, J. A. U.S. Pat. No. 4,873,356 1989.

EXAMPLE 4

(2-((Hydroxy(methyl)phosphinyl)methyl)-4-phenylbutanoyl)-L-leucine N-phenylamide

Step A: Benzyl 2-((hydroxy(methyl)phosphinyl) methyl)-4-phenylbutanoate (±)-Benzyl 2-((hydroxyphosphinyl)methyl)-4-phenylbutanoate (250 mg, 0.752 mmol) from Example 1 was dissolved in dichloromethane (1.0 mL) and molecular sieves (4 Å, 340 mg) were added. The mixture was cooled in an ice bath and diisopropylethylamine (0.150 mL, 111 mg, 0,861 mmol), O,N-bis(trimethylsilyl)acetamide (0.56 mL, 0.46 g, 2.3 mmol), and iodomethane (0.061 mL, 139 mg, 0.98 mmol) were added in sequence. The reaction mixture was allowed to warm to room temperature over 1 h and stirred for an additional 16 h. The mixture was diluted with ethyl acetate (25 mL) and washed with 2N aqueous hydrochloric acid (15 mL), water (15 mL), and saturated aqueous sodium chloride (15 mL). The aqueous layers were extracted in succession with ethyl acetate (25 mL) and the organic layers were dried (sodium sulfate), decanted, and evaporated to give 585 mg of orange oil containing the desired product. The crude product was purified by high pressure liquid chromatography on a 22 mm×25 cm reverse phase column (Whatman ODS-3, Partisil 10) eluting with 40% acetonitrile/60% water/0.05% trifluoroacetic acid (flow rate of 20 mL/min, detection at 250 nm). Evaporation of appropriate fractions gave 481 mg the desired product (84% yield) as a pale yellow viscous oil.

Step B: 2-((Hydroxy(methyl)phosphinyl)methyl)-4-phenylbutanoic acid

Benzyl 2-((hydroxy(methyl)phosphinyl)methyl)-4-phenylbutanoate (433 mg, 1.25 mmol) was dissolved in 95% ethanol (8.0 mL) and catalyst (130 mg of 10% palladium on carbon) was added. After being stirred under hydrogen (1 atm.) for 20 h at room temperature, the mixture was filtered through a 1-cm plug of Celite with additional 95% ethanol (2×10 mL). Evaporation of the filtrate gave 350 mg of a colorless oil used directly in Step C.

Step C: (2-((Hydroxy(methyl)phosphinyl)methyl)-4-phenylbutanoyl)-L-leucine N-phenylamide A portion (313 mg) of the crude 2-((hydroxy(methyl) phosphinyl)methyl)-4-phenylbutanoic acid from Step B was dissolved in tetrahydrofuran (3.0 mL) and 4 Å molecular sieves (0.40 g) were added. The mixture was stirred at room temperature and 1,1'-carbonyldiimidazole (215 mg, 1.33 mmol) was added, followed 15 min later by L-leucine N-phenylamide (297 mg, 1.44 mmol).[7] After 22 h, the mixture was diluted with ethyl acetate (30 mL) and washed with 2N aqueous hydrochloric acid (2×15 mL) and saturated aqueous sodium chloride (15 mL). The organic layer was dried (sodium sulfate) decanted, and evaporated to give 511 mg of colorless foam. The two diastereomers of a portion (145 mg) of the crude product were separated by high pressure liquid chromatography on a 22 mm×25 cm reverse phase column (Whatman ODS-3, Partisil 10) eluting with 60% methanol/40% water/0.05% trifluoroacetic acid (flow rate of 25 mL/min, detection at 250 nm). This yielded the more mobile isomer (43 mg, 31% yield for Steps B–C) and the less mobile isomer (51 mg, 36% yield for Steps B–C), both obtained as brittle films.

7 Weller, H. N.; Rom, M. B. *J. Enzyme Inhib.* 1988, 2, 183–193.

EXAMPLE 5

Preparation of [[Hydroxy[1(R)-[N-(N-acetyl-L-prolyl-L-alanyl)-amino]-ethyl]-phosphinyl]-methyl]-4-phenylbutanoyl-L-leucyl N-phenylamide

Step A: t-Butyl 2(R,S)-[[(R,S)-methoxy[1(R)-[N-(benzyloxycarbony)amino]-ethyl]phosphinyl] methyl]-4-phenylbutanoate To a solution of methyl 1(R)-[N-(benzyloxycarbonyl) amino]ethyl phosphinate (1.26 g, 4.92 mmol) in methanol at 0° C. was added methanolic sodium methoxide (25 wt. %, 1.18 mL, 5.16 mmol) dropwise with stirring over 30 min. A solution of t-butyl 2-methylene-4-phenylbutanoate (1.2 g, 5.16 mmol) in methanol (0.5 mL) was added slowly with cooling. The reaction mixture was stirred overnight at room temperature, quenched with 1N hydrochloric acid, and extracted four times with ethyl acetate. The combined organic layers-were washed with saturated brine solution, dried (magnesium sulfate), and evaporated. Purification was achieved by means of flash silica gel chromatography using 25% acetone in hexane as eluant; yield 1.58 g (65%).

Step B: 2(R,S)-[[(R,S)-Methoxy[1(R)-[N-(benzyloxycarbony)amino]-ethyl]phosphinyl]methyl]-4-phenylbutanoic acid t-Butyl 2(R,S)-[[(R,S)-methoxy[1(R)-[N-(benzyloxycarbony)amino]-ethyl]phosphinyl]methyl]-4-phenylbutanoate (1.51 g, 3.08 mmol) was dissolved in methylene chloride (15 mL), cooled to 0° C., and treated with trifluoroacetic acid (4.75 mL, 61.7 mmol) for 18 hours at 5° C. The reaction mixture was evaporated, coevaporated three times each with toluene and diethyl ether. The crude product was dried under high vacuum and used in Step C without further purification.

Step C: 2(R,S)-[[(R,S)-Methoxy[1(R)-[N-(benzyloxy carbony)amino]-ethyl]phosphinyl]methyl]-4-phenylbutanoyl-L-leucine-N-phenylamide The crude product from Step B was dissolved in tetrahydrofuran (8 mL). 1,1'-Carbonyldiimidazole (600 mg, 3.7 mmol) was added followed by L-leucine N-phenylamide (763 mg, 3.7 mmol). The reaction mixture was stirred at room temperature overnight, at which time additional 1,1'-carbonyldiimidazole (100 mg, 0.62 mmol) and L-leucine N-phenylamide (100 mg, 0.48 mmol) were added. After stirring at room temperature overnight, the reaction mixture was diluted with ethyl acetate (150 mL), washed twice with N hydrochloric acid, saturated brine solution, dried (magnesium sulfate), and evaporated. The crude product was treated with diazomethane in ether. The derived two-component product mixture was subjected to flash chromatography on silica gel using 25% acetone in hexane as eluant, followed by 30% and then 35% acetone in hexane; yield: higher Rf component (573 mg); lower Rf component (1.02 g); FAB MS: m/z 622 (M).

Step D: [[(R,S)-Methoxy[1(R)-[(aminoethyl)phosphinyl]methyl]-4-phenylbutanoyl-L-leucine-N-phenyl amide hydrochloride A solution of [[(R,S)-methoxy[1(R)-[N-(benzyloxycarbony)amino]-ethyl]phosphinyl]methyl]-4-phenylbutanoyl-L-leucine-N-phenylamide (lower Rf component from Step C) (67 mg, 0.11 mmol) in methanol (1 mL) containing acetyl chloride (8.4 µL) was stirred for 3 hours under an atmosphere of hydrogen in the presence of 20% palladium hydroxide-on-carbon (13 mg). The catalyst was removed by filtration through Celite, the filter washed with methanol, and the combined filtrate and washings evaporated and dried under high vacuum. The product was used directly in Step E.

Step E: [[(R,S)-Methoxy[1(R)-[N-(N-acetyl-L-prolyl-L-alanyl)-amino]-ethyl]-phosphinyl]-methyl]-4-phenylbutanoyl-L-leucine N-phenylamide To a solution of N-acetyl-L-Pro-L-Ala (91.3 mg, 0.40 mmol) in tetrahydrofuran (4 mL) cooled to 0° C. were added N-hydroxybenzotriazole (73.5 mg, 0.48 mmol) and N-methylmorpholine (66 µL, 0.60 mmol) followed by a suspension of [[(R,S)-methoxy[1(R)-[(aminoethyl)phosphinyl]methyl]-4-phenylbutanoyl-L-leucyl-anilide hydrochloride from Step D in tetrahydrofuran. 1-(-3-Dimethylaminopropyl)-3-ethylcarbodiimide hydrochloride (92 mg, 0.48 mmol) was then added, and the reaction mixture was stirred for 3 hours at 0° C. The reaction mixture was diluted with ethyl acetate, washed with N hydrochloric acid, water, saturated brine solution, dried (magnesium sulfate), and evaporated. The desired product was obtained by flash chromatography on silica gel using initially 2% methanol in methylene chloride and subsequently 5% methanol in methylene chloride; yield 58 mg (77%); FAB MS: m/z 737 (M+1+K). The 200 MHz NMR spectrum in methanol-$d_4$ was in accord with the desired structure.

Step F: [[Hydroxy[1(R)-[N-(N-acetyl-L-prolyl-L-alanyl)-amino]-ethyl]-phosphinyl]-methyl]-4-phenylbutanoyl-L-leucine N-phenylamide A solution of [[(R,S)-Methoxy[1(R)-[N-(N-acetyl-L-prolyl-L-alanyl)-amino]-ethyl]-phosphinyl]methyl]-4-phenylbutanoyl-L-leucyl N-phenylamide (58 mg, 0.096 mmol) in methanol (0.5 mL) was treated with 2N aqueous sodium hydroxide (0.25 mL) for 4 hours at room temperature. The mixture was evaporated, dissolved in water, acidified to pH~1 with 2N hydrochloric acid, and extracted 4 times with ethyl acetate. The combined organic extracts were washed with saturated brine solution, dried (magnesium sulfate), and evaporated.

Purification was effected by reverse phase-high performance liquid chromatography using a Waters Prep Nova-Pak HR C18 6 mm column (19×300 mm) (detection at 220 nm; mobile phase: 35% acetonitrile containing 0.1% trifluoroacetic acid-65% water containing 0.1% trifluoroacetic acid; flow rate: 20 mL/min). Evaporation of appropriate fractions gave desired product as an amorphous solid; FAB MS: m/z 684 (M+1), 706 (M+Na), 722 (M+K). The 200 MHz NMR spectrum in methanol-$d_4$ was in accord with the desired structure.

EXAMPLE 6

[Hydroxy-[N-(N-(benzoyl)-L-prolyl)aminobutyl]phosphinyl]methyl]-4-phenylbutanoyl-L-leucine N-phenylamide Step A: [[(R,S)-Methoxy-[N-(N-(benzyloxycarbonyl)-L-prolyl)aminobutyl]phosphinyl]methyl]-4-phenylbutanoyl-L-leucine N-phenylamide To a suspension of N-(benzyloxycarbonyl)-L-Pro (191 mg, 0.767 mmol) in dry methylene chloride (5 mL) cooled to 0° C. were added N-hydroxybenzotriazole (141 mg, 0.92 mmol), N-methylmorpholine (101 µL, 0.92 mmol), and 2-(((4-aminobutyl)methoxyphosphinyl)methyl)-4-phenylbutanoyl)-L-leucine N-phenylamide. After five min., the ice bath was removed, and the mixture was stirred for 20 min at room temperature. 1-(-3-Dimethylaminopropyl)-3-ethylcarbodiimide hydrochloride (176 mg, 0.92 mmol) was then added and the reaction mixture was stirred for 5 hours at room temperature. After dilution with ethyl acetate (75 mL), the mixture was washed twice with 2N hydrochloric acid, saturated sodium hydrogencarbonate solution, saturated brine solution, dried (magnesium sulfate), and evaporated. Purification was achieved by flash chromatography on silica gel using initially 2% methanol in methylene chloride and subsequently 3% methanol in methylene chloride; yield 170 mg; FAB MS: m/z 747 (M+1), 769 (M+Na).

Step B: [[(R,S)-Methoxy-[N-(N-(benzoyl)-L-prolyl) aminobutyl]phosphinyl]methyl]-4-phenylbutanoyl-L-leucine N-phenylamide A solution of [[(R,S)-methoxy-[N-(N-(benzyloxycarbonyl)-L-prolyl)aminobutyl]phosphinyl] methyl]-4-phenylbutanoyl-L-leucine N-phenylamide (169 mg, 0.226 mmol) in methanol (2 mL) was stirred for 6 hours under an atmosphere of hydrogen in the presence of 20% palladium hydroxide-on-carbon (34 mg). The catalyst was removed by filtration through Celite, the filter washed with methanol, and the combined filtrate and washings evaporated. The resulting amine was dried under high vacuum, then dissolved in methylene chloride (2 mL), cooled to 0° C. and treated with benzoyl chloride (29 ml, 0.25 mmol) and N-methylmorpholine (27 µl, 0.25 mmol) at 0° C. for 90 min. The reaction mixture was diluted with ethyl acetate (25 mL), washed with 2N hydrochloric acid, saturated brine solution, dried (magnesium sulfate), and evaporated. Purification was achieved by flash chromatography on silica gel using initially 2% methanol in methylene chloride and subsequently 3% methanol in methylene chloride; yield 101 mg (62%); FAB MS: m/z 716 (M+1).

Step C: [[Hydroxy-[N-(N-(benzoyl)-L-prolyl) aminobutyl]phosphinyl]methyl]-4-phenylbutanoyl-L-leucine N-phenylamide A solution of [[(R,S)-methoxy-[N-(N-(benzoyl)-L-prolyl) aminobutyl]phosphinyl]methyl]-4-phenylbutanoyl-L-leucine N-phenylamide (101 mg, 0.14 mmol) in methanol (1 mL) was treated with 2N aqueous sodium hydroxide (0.5 mL) for 3 hours at room temperature. Additional 2N aqueous sodium hydroxide (0.5 mL) was then added, and the mixture was stirred overnight at room temperature. The solvent was removed by evaporation, and the residue was dissolved in water (25 mL). The aqueous solution was extracted with diethyl ether, acidified to ~pH 1 with 6N hydrochloric acid, and extracted with ethyl acetate (3×). The combined organic layers were washed With saturated brine solution, dried (magnesium sulfate), and evaporated. Purification was effected by reverse phase-high performance liquid chromatography using a Waters Prep Nova-Pak HR C18 6 mm column (19×300 mm) (detection at 220 nm; mobile phase: 57% acetonitrile containing 0.1% trifluoroacetic acid-43% water containing 0.1% trifluoroacetic acid; flow rate: 20 mL/min). Evaporation of appropriate fractions gave desired product as an amorphous solid; yield 47 mg; FAB-MS: m/z 703 (M+1),725 (M+Na), 741 (M+K). The 200 MHz NMR spectrum in methanol-$d_4$ was in accord with the desired structure.

EXAMPLE 7

[Hydroxy-[2-Methylpropyloxycarbonylaminobutyl] phosphinyl]methyl]-4-phenylbutanoyl-L-leucine N-phenylamide Step A: [[(R,S)-Methoxy-[2-Methylpropyloxycarbonylaminobutyl]phosphinyl] methyl]-4-phenylbutanoyl-L-leucine N-phenylamide 2-(((4-aminobutyl)methoxyphosphinyl)methyl)-4-phenylbutanoyl)-L-leucine N-phenylamide (0.155 mmol) was dissolved in 5 mL of dry methylene chloride under nitrogen at 0° C. and to it 0.03 mL (0.233 mmol of isobutyl chloroformate and 0.07 mL of diisopropylethylamine were added. The reaction mixture was slowly brought to room temperature and stirred for 3 hrs. After dilution with ethyl acetate (75 mL), the mixture was washed twice with 2N hydrochloric acid, saturated sodium hydrogencarbonate solution, saturated brine solution, dried (magnesium sulfate), and evaporated. Purification was achieved by flash chromatography on silica gel using 10% methanol in chloroform; yield 83 mg.

Step B: [[Hydroxy-[2-Methylpropyloxycarbonylaminobutyl]phosphinyl] methyl]-4-phenylbutanoyl-L-leucine N-phenylamide A solution of [[(R,S)-methoxy-[2-Methylpropyloxycarbonylaminobutyl]phosphinyl]methyl]-4-phenylbutanoyl-L-leucine N-phenylamide (81 mg) in methylene chloride (3 mL) was treated with 0.16 mL of trifluoroacetic acid at 0° C. under nitrogen and was stirred overnight at room temperature. The solvent was removed by coevaporation with 10 mL of toluene (3×) and the residue was purified by reverse phase-high performance liquid chromatography using a Waters Prep Nova-Pak HR C18 6 mm column (19×300 mm). (detection at 220 nm; mobile phase: 45% acetonitrile containing 0.1% trifluoroacetic acid-55% water containing 0.1% trifluoroacetic acid; flow rate: 20 mL/min). Evaporation of appropriate fractions gave desired product as an amorphous solid; yield 46 mg; FAB MS: m/z 608 (M+Li),624 (M+Na), 640 (M+K). The 200 MHz NMR spectrum in methanol-$d_4$ was in accord with the desired structure.

EXAMPLE 8

[Hydroxy-[1-Methylethylaminocarbonylaminobutyl] phosphinyl]methyl]-4-phenylbutanoyl-L-leucine N-phenylamide Step A: [[(R,S)-Methoxy-[1-Methylethylaminocarbonylaminobutyl]phosphinyl] methyl]-4-phenylbutanoyl-L-leucine N-phenylamide 2-(((4-aminobutyl)methoxyphosphinyl)methyl)-4-phenylbutanoyl)-L-leucine N-phenylamide.(0.155 mmol) was dissolved in 5 mL of dry methylene chloride under nitrogen at 0° C. and to it was added 0.075 mL of isopropyl isocyanate. The reaction mixture was slowly brought to room temperature and stirred for 2 hours. After dilution with ethyl acetate (75 mL), the mixture was washed twice with 2N hydrochloric acid, saturated sodium hydrogencarbonate solution, saturated brine solution, dried (magnesium sulfate), and evaporated. Purification was achieved by flash chromatography on silica gel using 5% methanol, 20% acetone in methylene chloride; yield 195 mg.

Step B: [[Hydroxy-[1-Methylethylaminocarbonylaminobutyl]phosphinyl] methyl]-4-phenylbutanoyl-L-leucine N-phenylamide A solution of [[(R,S)-methoxy-[1-Methylethylaminocarbonylaminobutyl]phosphinyl]methyl]-4-phenylbutanoyl-L-leucine N-phenylamide (181 mg) in methanol (3 mL) was treated with 2N aqueous sodium hydroxide (1 mL) for 3 hours at room temperature. Additional 2N aqueous sodium hydroxide (0.5 mL) was then added, and the mixture was stirred overnight at room temperature. The solvent was removed by evaporation, and the residue was dissolved in water (25 mL). The aqueous solution was extracted with diethyl ether, acidified to pH ~1 with 6N hydrochloric acid, and extracted with ethyl acetate (3×). The combined organic layers were washed with saturated brine solution, dried (magnesium sulfate), and evaporated. Purification was effected by reverse phase-high performance liquid chromatography using a Waters Prep Nova-Pak HR C18 6 μm column (19×300 mm) (detection at 22 nm; mobile phase: 55% acetonitrile containing 0.1% trifluoroacetic acid-45% water containing 0.1% trifluoroacetic acid; flow rate: 20 mL/min). Evaporation of appropriate fractions gave desired product as an amorphous solid; yield 103 mg; FAB MS: m/z 587 (M+1), 609 (M+Na), 625(M+K). The 200 MHz NMR spectrum in methanol-$d_4$ was in accord with the desired structure.

What is claimed:
1. A compound of formula I

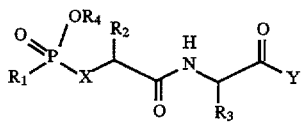

or a pharmaceutically acceptable salt thereof wherein:

$R_1$ is substituted $C_{1-6}$alkyl, wherein the substituent is selected from the group consisting of:
(a) hydrogen,
(b) —C(O)NH$_2$,
(c) —C(O)NHC$_{1-6}$alkyl,
(d) —C(O)N(C$_{1-6}$alkyl)$_2$,
(e) —C(O)N(C$_{1-6}$alkyl)aryl or —C(O)N(C$_{1-6}$alkyl)arylC$_{1-6}$alkyl,
(f) —C(O)NHaryl or —C(O)NHarylC$_{1-6}$alkyl, wherein the aryl group is selected from the group consisting of
(1) phenyl,
(2) naphthyl,
(3) pyridyl,
(4) furyl,
(5) pyrryl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl, and
(23) benzoxazolyl,
(24) isoxazolyl, and
(25) benzthiazolyl,
and mono and di-substituted aryl as defined above in items (1) to (25), wherein the substitutents are independently hydrogen, $C_{1-6}$alkyl, $C_{1-6}$alkyloxy, halo, hydroxy, $C_{1-6}$alkylcarbonyl, carboxy;

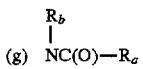

wherein $R_a$ and $R_b$ are each independently hydrogen, NHC$_{1-6}$alkyl, NHC$_{6-10}$aryl, NHC$_{6-10}$arylC$_{1-6}$alkyl, OC$_{1-6}$alkyl, OC$_{6-10}$aryl, OC$_{6-10}$arylC$_{1-6}$alkyl, C$_{6-10}$aryl or C$_{6-10}$aryl-C$_{1-6}$alkyl, wherein the aryl may be mono or di-substituted as defined above; or substituted C$_{1-6}$alkyl wherein the substitutent is selected from hydroxy and halo, provided that when $R_b$ is hydrogen, $R_a$ is other than C$_{6-10}$aryl or C$_{6-10}$aryl-C$_{1-6}$alkyl,
(h) —NH—R$_e$—R$_f$—R$_g$
wherein R$_e$ is a single bond or an amino acid of the formula

or

R$_e$ is selected from the group consisting of glycine, alanine, leucine, isoleucine, norleucine, phenylalanine, tyrosine, lysine, arginine, histidine, aspartic acid, asparagine, glutamic acid, glutamine, serine, and threonine;

R$_f$ is a single bond, or R$_f$ is an amino acid of the formula

provided that when

R$_e$ is an amino acid, R$_f$ is other than an amino acid, wherein Z and Z' are each independently selected from the group consisting of
(a) hydrogen,
(b) C$_{1-6}$alkyl,
(c) mercapto C$_{1-6}$alkyl,
(d) hydroxy C$_{1-6}$alkyl,
(e) carboxy C$_{1-6}$alkyl,
(f) amino C$_{1-6}$alkyl,
(g) aminocarbonyl C$_{1-6}$alkyl,
(h) mono- or di-C$_{1-6}$alkyl amino C$_{1-6}$alkyl,
(i) guanidino C$_{1-6}$alkyl,
(j) substituted phenyl C$_{1-6}$alkyl, wherein the substitutent is hydrogen, hydroxy, carboxy, or C$_{1-4}$alkyl,
(k) substituted indolyl C$_{1-6}$alkyl, wherein the substitutent is hydrogen, hydroxy, carboxy, or C$_{1-4}$alkyl,
(l) substituted imidazolyl C$_{1-6}$alkyl wherein the substitutent is hydrogen, hydroxy, carboxy, or C$_{1-4}$alkyl;
or
R$_f$ is selected from the group consisting of glycine, alanine, proline;

R$_g$ is acetyl, benzoyl, benzyloxycarbonyl, p-toluenesulfonyl, or t-butyloxycarbonyl;

R$_2$ is CH$_2$R$_i$ wherein
R$_i$ is aryl —C$_{0-2}$alkyl or substituted aryl C$_{0-2}$alkyl wherein the substituent is C$_{1-3}$alkyl or hydroxy, and wherein the aryl group is independently selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,

(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl, and
(23) isoxazolyl,
and mono and di-substituted aryl as defined above in items (1) to (23) wherein the substitutents are independently $C_{1-6}$alkyl, halo, hydroxy, and $C_{1-6}$alkylcarbonyl;

$R_3$ is $C_{1-4}$alkyl;

$R_4$ is
(a) H,
(b) $CH(R_j)O—C(O)—R_k$;
wherein $R_j$ is hydrogen, $C_{1-6}$alkyl and $R_k$ is $C_{1-6}$alkyl, X is $CH_2$; and Y is Y is $-\underset{\underset{R_6}{|}}{N}-R_6$ 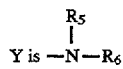

wherein
$R_5$ and $R_6$ are each individually selected from the group consisting of
(a) H,
(b) $C_{1-10}$alkyl,
(c) aryl or aryl$C_{1-6}$alkyl,
wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl, and
(25) benzoxazolyl;
and aryl and mono and di-substituted aryl as defined above in items (1) to (25) wherein the substitutents are independently $C_{1-6}$alkyl, halo, hydroxy, $C_{1-6}$alkyloxy, $C_{1-6}$alkylcarbonyl, carboxy and $C_{1-6}$alkylcarbonyloxy.

2. A compound according to claim 1 wherein:
$R_1$ is $C_{1-6}$alkyl or substituted $C_{1-6}$alkyl, wherein the substituent is selected from the group consisting of:
a) hydrogen,
b) $—C(O)NH_2$,
c) $C(O)NH$-aryl or aryl $C_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl, and
(9) indolyl,
and mono and di-substituted aryl as immediately defined in definitions (1) to (9) above wherein the substitutents are independently $C_{1-6}$alkyl, halo, hydroxy, and carbonyl$C_{1-6}$alkyl, carboxy;

(d) $\underset{\underset{|}{N}}{R_b}-C(O)-R_a$ 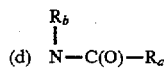

wherein
$R_a$ and $R_b$ are each independently hydrogen, aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
and mono and di-substituted aryl as defined in items (1) to (9) above; or substituted $C_{1-6}$alkyl wherein the substitutent is selected from hydroxy and halo;
e) $—NH—R_e—R_f—R_g$ 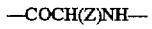
wherein Re is an amino acid of the formula $—COCH(Z)NH—$ or is selected from the group consisting of glycine, alanine, leucine, isoleucine, norleucine, phenylalanine, tyrosine, lysine, arginine, histidine, aspartic acid, asparagine, glutamic acid, glutamine, serine, threonine;

$R_f$ is a single bond
wherein Z is each independently selected from the group consisting of
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino $C_{1-6}$alkyl,
(g) aminocarbonyl $C_{1-6}$alkyl,
(h) mono- or di-$C_{1-6}$alkyl amino $C_{1-6}$alkyl,
(i) guanidino $C_{1-6}$alkyl,
(j) substituted phenyl $C_{1-6}$alkyl, wherein the substitutent is hydrogen, hydroxy, carboxy, or $C_{1-4}$alkyl,
(k) substituted indolyl $C_{1-6}$alkyl, wherein the substitutent is hydrogen, hydroxy, carboxy, or $C_{1-4}$alkyl,
(l) substituted imidazolyl $C_{1-6}$alkyl wherein the substitutent is hydrogen, hydroxy, carboxy, or $C_{1-4}$alkyl; or
is selected from the group consisting of glycine, alanine, and proline;

$R_g$ is acetyl, benzoyl, benzyloxy-carbonyl, p-toluenesulfony, or t-butyloxycarbonyl.

3. A compound according to claim 2 wherein, $R_2$ is $CH_2R_i$ wherein
  $R_i$ is aryl $C_{0-2}$alkyl or substituted aryl $C_{0-2}$alkyl wherein the substituent is $C_{1-3}$alkyl or hydroxy, and wherein the aryl group in is independently selected from the group consisting of
  (1) phenyl,
  (2) naphthyl,
  (3) thienyl,
  (4) imidazolyl,
  (5) benzimidazolyl,
  (6) pyrimidyl,
  (7) benzofuryl,
  (8) benzothienyl,
  (9) indolyl,
and mono and di-substituted aryl as defined above in items (1) to (9) wherein the substitutents are independently $C_{1-6}$alkyl, halo, hydroxy, and $C_{1-6}$alkylcarbonyl.

4. A compound according to claim 3 wherein, $R_3$ is $C_{1-4}$alkyl;
$R_4$ is
  (a) H,
  (b) $CH(R_j)O\text{—}C(O)\text{—}R_k$,
wherein
$R_j$ is $C_{1-6}$alkyl, and
$R_k$ is $C_{1-6}$alkyl.

5. A compound according to claim 4 wherein,
X is $CH_2$; and
Y is

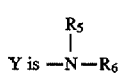

wherein
$R_5$ is hydrogen, and
$R_6$ are each individually selected from the group consisting of
  (a) $C_{1-10}$alkyl, or
  (c) aryl or aryl$C_{1-6}$alkyl,
  wherein the aryl group is selected from the group consisting of
  (1) phenyl,
  (2) naphthyl,
  (3) thienyl,
  (4) imidazolyl,
  (5) benzimidazolyl,
  (6) pyrimidyl,
  (7) benzofuryl,
  (8) benzothienyl,
  (9) indolyl,
  (10) pyridyl.

6. A compound according to claim 5 wherein:
$R_1$ is substituted $C_{1-6}$alkyl, wherein the substituent is selected from the group consisting of:

a) hydrogen,

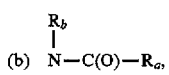

(c) —NH—$R_e$—$R_f$—$R_g$
wherein Re is an amino acid selected from the group consisting of glycine, alanine, leucine, isoleucine, norleucine, phenylalanine, tyrosine, lysine, arginine, histidine, aspartic acid, asparagine, glutamic acid, glutamine, serine, threonine;

$R_f$ is a single bond;
$R_g$ is acetyl, benzoyl, benzyloxy-carbonyl, p-toluenesulfony, or t-butyloxycarbonyl.

7. A compound according to claim 6 wherein, $R_1$ is substituted $C_{1-4}$alkyl, wherein the substituent is selected from the group consisting of:

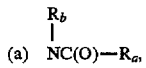

(b) —NH—$R_e$—$R_f$—$R_g$
wherein
$R_e$ is a single bond or an amino acid selected from the group consisting of glycine, alanine, leucine, isoleucine, norleucine, phenylalanine, tyrosine, lysine, arginine, histidine, aspartic acid, asparigine, glutamic acid, glutamine, serine, threonine;

$R_f$ is a single bond;
$R_g$ is acetyl, benzoyl, benzyloxy-carbonyl, p-toluenesulfonyl or t-butyloxycarbonyl.

8. A compound according to claim 7 wherein, $R_2$ is $CH_2R_i$ wherein
  $R_i$ is aryl $C_{1-2}$alkyl wherein the aryl group is selected from the group consisting of
  (1) phenyl,
  (2) naphthyl,
  (3) thienyl, and
  (4) imidazolyl;

$R_3$ is $C_{1-4}$alkyl;
$R_4$ is
  (a) H,
  (b) $CH(R_j)O\text{—}C(O)\text{—}R_k$,
wherein
$R_j$ is $C_{1-6}$alkyl, and
$R_k$ is $C_{1-6}$alkyl;
X is $CH_2$; and
Y is

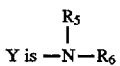

wherein
$R_5$ is hydrogen, and
$R_6$ is aryl wherein the aryl group is selected from the group consisting of
  (1) phenyl,
  (2) naphthyl,
  (3) thienyl, and
  (4) imidazolyl.

9. A compound selected from
  (a) (2-(((4-(1,3-Dihydro-1,3-dioxo-2H-isoindol-2-yl) butyl)hydroxyphosphinyl)methyl)-4-phenylbutanoyl)-L-leucine N-phenylamide;
  (b) (2-(((4-(1,3-Dihydro-1-oxo-2H-isoindol-2-yl) butyl) hydroxyphosphinyl)methyl)-4-phenylbutanoyl)-L-leucine N-phenylamide;
  (c) (2-(((4-(1,3-Dihydro-1-oxo-2H-isoindol-2-yl) butyl) (2-methyl-1-(1-oxopropoxy)propoxy)phosphinyl) methyl)-4-phenylbutanoyl)-L-leucine N-phenylamide;
  (d) (2-((Hydroxy(methyl)phosphinyl)methyl)-4-phenylbutanoyl)-L-leucine N-phenylamide; or (e) ((Hydroxy(1(R)-(N-(N-acetyl-L-proyl-L-alanyl)-amino)ethyl)-phosphinyl)methyl)-4-phenylbutanoyl-L-leucine N-phenylamide.

10. A pharmaceutical composition for inhibiting stromelysin comprising a pharmaceutically carrier and a non-toxic effective amount of compound of Formula I according to claim 1.

11. A pharmaceutical composition for treating arthritis comprising a pharmaceutical carder and a non-toxic effective amount of compound of Formula I according to claim 1.

12. A method of inhibiting stromelysin in a patient having a stromelysin mediated disease, comprising:
   administration to said patient of a therapeutically effective amount of compound of Formula I according to claim 1.

13. A method of treating arthritis in a pateint having arthritis comprising:
   administration to said patient a therapeutically effective amount of compound of Formula I according to claim 1.

14. A compound of formula I

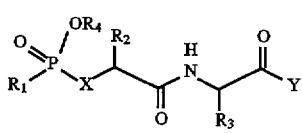

or a pharmaceutically acceptable salt thereof wherein:
$R_1$ is substituted $C_{1-6}$alkyl, wherein the substituent is selected from the group consisting of:
(a) hydrogen,
(b) —C(O)NH$_2$,
(c) —C(O)NHC$_{1-6}$alkyl,
(d) —C(O)N(C$_{1-6}$alkyl)$_2$,
(e) —C(O)N(C$_{1-6}$alkyl)aryl or —C(O)N(C$_{1-6}$alkyl)arylC$_{1-6}$alkyl,
(f) —C(O)NHaryl or —C(O)NHarylC$_{1-6}$alkyl,
   wherein the aryl group is selected from the group consisting of
   (1) phenyl,
   (2) naphthyl,
   (3) pyridyl,
   (4) furyl,
   (5) pyrryl,
   (6) thienyl,
   (7) isothiazolyl,
   (8) imidazolyl,
   (9) benzimidazolyl,
   (10) tetrazolyl,
   (11) pyrazinyl,
   (12) pyrimidyl,
   (13) quinolyl,
   (14) isoquinolyl,
   (15) benzofuryl,
   (16) isobenzofuryl,
   (17) benzothienyl,
   (18) pyrazolyl,
   (19) indolyl,
   (20) isoindolyl,
   (21) purinyl,
   (22) carbazolyl, and
   (23) benzoxazolyl,
   (24) isoxazolyl, and
   (25) benzthiazolyl,
and mono and di-substituted aryl as defined above in items (1) to (25), wherein the substitutents are independently hydrogen, $C_{1-6}$alkyl, $C_{1-6}$alkyloxy, halo, hydroxy, $C_{1-6}$alkylcarbonyl, carboxy;

(g) 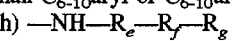

wherein
$R_a$ and $R_b$ are each independently hydrogen, NHC$_{1-6}$alkyl, NHC$_{6-10}$aryl, NHC$_{6-10}$arylC$_{1-6}$alkyl, OC$_{1-6}$alkyl, OC$_{6-10}$aryl, OC$_{6-10}$aryl-C$_{1-6}$alkyl, C$_{6-10}$aryl or C$_{6-10}$aryl-C$_{1-6}$alkyl, wherein the aryl may be mono or di-substituted as defined above; or substituted C$_{1-6}$alkyl wherein the substitutent is selected from hydroxy and halo, provided that when $R_b$ is hydrogen, $R_a$ is other than C$_{6-10}$aryl or C$_{6-10}$aryl-C$_{1-6}$alkyl, (h) —NH—R$_e$—R$_f$—R$_g$
wherein
$R_e$ is a single bond or an amino acid of the formula

or
$R_e$ is selected from the group consisting of glycine, alanine, leucine, isoleucine, norleucine, phenylalanine, tyrosine, lysine, arginine, histidine, aspartic acid, asparagine, glutamic acid, glutamine, serine, and threonine;

$R_f$ is a single bond, or $R_f$ is an amino acid of the formula

provided that when
$R_e$ is an amino acid, $R_f$ is other than an amino acid, wherein Z and Z' are each independently selected from the group consisting of
(a) hydrogen,
(b) C$_{1-6}$alkyl,
(c) mercapto C$_{1-6}$alkyl,
(d) hydroxy C$_{1-6}$alkyl,
(e) carboxy C$_{1-6}$alkyl,
(f) amino C$_{1-6}$alkyl,
(g) aminocarbonyl C$_{1-6}$alkyl,
(h) mono- or di-C$_{1-6}$alkyl amino C$_{1-6}$alkyl,
(i) guanidino C$_{1-6}$alkyl,
(j) substituted phenyl C$_{1-6}$alkyl, wherein the substitutent is hydrogen, hydroxy, carboxy, or C$_{1-4}$alkyl,
(k) substituted indolyl C$_{1-6}$alkyl, wherein the substitutent is hydrogen, hydroxy, carboxy, or C$_{1-4}$alkyl,
(l) substituted imidazolyl C$_{1-6}$alkyl wherein the substitutent is hydrogen, hydroxy, carboxy, or C$_{1-4}$alkyl;
or
$R_f$ is selected from the group consisting of glycine, alanine, proline;
$R_g$ is acetyl, benzoyl, benzyloxycarbonyl, p-toluenesulfonyl, or t-butyloxycarbonyl;
$R_2$ is —CH$_2$CH$_2$aryl
   wherein the aryl group is independently selected from the group consisting of
   (1) phenyl,
   (2) naphthyl,
   (3) pyridyl,
   (4) pyrryl,
   (5) furyl,
   (6) thienyl,
   (7) isothiazolyl,
   (8) imidazolyl, (9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl, and
(23) isoxazolyl, and mono and di-substituted aryl as defined above in items (1) to (23) wherein the substitutents are independently $C_{1-6}$alkyl, halo, hydroxy, and $C_{1-6}$alkylcarbonyl;

$R_3$ is $C_{1-4}$alkyl;

$R_4$ is
(a) H,
(b) $CH(R_j)O-C(O)-R_k$;

wherein $R_j$ is hydrogen, $C_{1-6}$alkyl and $R_k$ is $C_{1-6}$alkyl,

X is $CH_2$; and

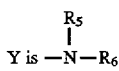

Y is $-N-R_6$ wherein $R_5$ and $R_6$ are each individually selected from the group consisting of
(a) H,
(b) $C_{1-10}$alkyl,
(c) aryl or aryl$C_{1-6}$alkyl, wherein the aryl group is selected from the group consisting of
(1) phenyl,
(2) naphthyl,
(3) pyridyl,
(4) pyrryl,
(5) furyl,
(6) thienyl,
(7) isothiazolyl,
(8) imidazolyl,
(9) benzimidazolyl,
(10) tetrazolyl,
(11) pyrazinyl,
(12) pyrimidyl,
(13) quinolyl,
(14) isoquinolyl,
(15) benzofuryl,
(16) isobenzofuryl,
(17) benzothienyl,
(18) pyrazolyl,
(19) indolyl,
(20) isoindolyl,
(21) purinyl,
(22) carbazolyl,
(23) isoxazolyl,
(24) benzthiazolyl, and
(25) benzoxazolyl;

and aryl and mono and di-substituted aryl as defined above in items (1) to (25) wherein the substitutents are independently $C_{1-6}$alkyl, halo, hydroxy, $C_{1-6}$alkyloxy, $C_{1-6}$alkylcarbonyl, carboxy and $C_{1-6}$alkylcarbonyloxy.

15. A compound according to claim 14 wherein:

$R_1$ is $C_{1-6}$alkyl or substituted $C_{1-6}$alkyl, wherein the substituent is selected from the group consisting of:
a) hydrogen,
b) $-C(O)NH_2$,
c) $C(O)NH$-aryl or aryl $C_{1-6}$alkyl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl, and
(9) indolyl, and mono and di-substituted aryl as immediately defined in definitions (1) to (9) above wherein the substitutents are independently $C_{1-6}$alkyl, halo, hydroxy, and carbonyl$C_{1-6}$alkyl, carboxy;

(d)

wherein $R_a$ and $R_b$ are each independently hydrogen, aryl wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl, and mono and di-substituted aryl as defined in items (1) to (9) above; or substituted $C_{1-6}$alkyl wherein the substitutent is selected from hydroxy and halo;
e) $-NH-R_e-R_f-R_g$ wherein $R_e$ is an amino acid of the formula

$-COCH(Z)NH-$ or is selected from the group consisting of glycine, alanine, leucine, isoleucine, norleucine, phenylalanine, tyrosine, lysine, arginine, histidine, aspartic acid, asparagine, glutamic acid, glutamine, serine, threonine;

$R_f$ is a single bond wherein

Z is each independently selected from the group consisting of
(a) hydrogen,
(b) $C_{1-6}$alkyl,
(c) mercapto $C_{1-6}$alkyl,
(d) hydroxy $C_{1-6}$alkyl,
(e) carboxy $C_{1-6}$alkyl,
(f) amino $C_{1-6}$alkyl,
(g) aminocarbonyl $C_{1-6}$alkyl,
(h) mono- or di-$C_{1-6}$alkyl amino $C_{1-6}$alkyl,
(i) guanidino $C_{1-6}$alkyl,
(j) substituted phenyl $C_{1-6}$alkyl, wherein the substitutent is hydrogen, hydroxy, carboxy, or $C_{1-4}$alkyl,
(k) substituted indolyl $C_{1-6}$alkyl, wherein the substitutent is hydrogen, hydroxy, carboxy, or $C_{1-4}$alkyl, (l) substituted imidazolyl $C_{1-6}$alkyl wherein the substitutent is hydrogen, hydroxy, carboxy, or $C_{1-4}$alkyl; or is selected from the group consisting of glycine, alanine, and proline;

$R_g$ is acetyl, benzoyl, benzyloxy-carbonyl, p-toluenesulfony, or t-butyloxycarbonyl.

16. A compound according to claim 15 wherein, $R_2$ is —$CH_2CH_2$aryl wherein
wherein the aryl group in is independently selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
and mono and di-substituted aryl as defined above in items (1) to (9) wherein the substitutents are independently $C_{1-6}$alkyl, halo, hydroxy, and $C_{1-6}$alkylcarbonyl.

17. A compound according to claim 16 wherein, $R_3$ is $C_{1-4}$alkyl;

$R_4$ is
(a) H,
(b) $CH(R_j)O$—$C(O)$—$R_k$,
wherein
$R_j$ is $C_{1-6}$alkyl, and
$R_k$ is $C_{1-6}$alkyl.

18. A compound according to claim 17 wherein,
X is $CH_2$; and

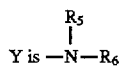

wherein
$R_5$ is hydrogen, and
$R_6$ are each individually selected from the group consisting of
(a) $C_{1-10}$alkyl, or
(c) aryl or aryl$C_{1-6}$alkyl,
wherein the aryl group is selected from the group consisting of
(1) phenyl,
(2) naphthyl,
(3) thienyl,
(4) imidazolyl,
(5) benzimidazolyl,
(6) pyrimidyl,
(7) benzofuryl,
(8) benzothienyl,
(9) indolyl,
(10) pyridyl.

19. A compound according to claim 18 wherein:

$R_1$ is substituted $C_{1-6}$alkyl, wherein the substituent is selected from the group consisting of:
(a) hydrogen

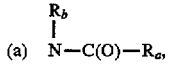

(c) —NH—$R_e$—$R_f$—$R_g$

wherein $R_e$ is an amino acid selected from the group consisting of glycine, alanine, leucine, isoleucine, norleucine, phenylalanine, tyrosine, lysine, arginine, histidine, aspartic acid, asparagine, glutamic acid, glutamine, serine, threonine;

$R_f$ is a single bond;

$R_g$ is acetyl, benzoyl, benzyloxy-carbonyl, p-toluenesulfony, or t-butyloxycarbonyl.

20. A compound according to claim 19 wherein, $R_1$ is substituted $C_{1-4}$alkyl, wherein the substituent is selected from the group consisting of:

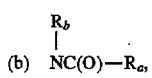

(b) —NH—$R_e$—$R_f$—$R_g$

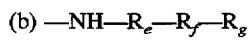

wherein $R_e$ is a single bond or an amino acid selected from the group consisting of glycine, alanine, leucine, isoleucine, norleucine, phenylalanine, tyrosine, lysine, arginine, histidine, aspartic acid, asparigine, glutamic acid, glutamine, serine, threonine;

$R_f$ is a single bond;

$R_g$ is acetyl, benzoyl, benzyloxy-carbonyl, p-toluenesulfonyl or t-butyloxycarbonyl.

21. A compound according to claim 20 wherein, $R_2$ is $CH_2CH_2$aryl wherein
wherein the aryl group is selected from the group consisting of
(1) phenyl,
(2) naphthyl,
(3) thienyl, and
(4) imidazolyl;

$R_3$ is $C_{1-4}$alkyl;

$R_4$ is
(a) H,
(b) $CH(R_j)O$—$C(O)$—$R_k$,
wherein $R_j$ is $C_{1-6}$alkyl, and $R_k$ is $C_{1-6}$alkyl;

X is $CH_2$; and

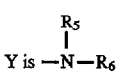

wherein $R_5$ is hydrogen, and $R_6$ is aryl wherein the aryl group is selected from the group consisting of
(1) phenyl,
(2) naphthyl,
(3) thienyl, and
(4) imidazolyl.

* * * * *